US010213385B2

(12) United States Patent
Yang et al.

(10) Patent No.: US 10,213,385 B2
(45) Date of Patent: *Feb. 26, 2019

(54) COMBINATIONAL LIPOSOME COMPOSITIONS FOR CANCER THERAPY

(71) Applicant: MALLINCKRODT LLC, Hazelwood, MO (US)

(72) Inventors: Jun Yang, Ballwin, MO (US); Stephen H. Wu, Chesterfield, MO (US); Cliff J. Herman, St. Louis, MO (US)

(73) Assignee: MALLINCKRODT LLC, Hazelwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/663,472

(22) Filed: Jul. 28, 2017

(65) Prior Publication Data

US 2018/0015039 A1 Jan. 18, 2018

Related U.S. Application Data

(63) Continuation of application No. 15/162,072, filed on May 23, 2016, now Pat. No. 9,717,686, which is a (Continued)

(51) Int. Cl.
*A61K 9/12* (2006.01)
*A61K 9/127* (2006.01)
*A61K 31/282* (2006.01)
*A61K 33/24* (2006.01)
*A61K 31/337* (2006.01)
*A61K 31/513* (2006.01)
*A61K 31/555* (2006.01)
(Continued)

(52) U.S. Cl.
CPC .......... *A61K 9/1273* (2013.01); *A61K 9/0019* (2013.01); *A61K 9/127* (2013.01); *A61K 9/1272* (2013.01); *A61K 31/282* (2013.01); *A61K 31/337* (2013.01); *A61K 31/513* (2013.01); *A61K 31/555* (2013.01); *A61K 31/704* (2013.01); *A61K 31/7068* (2013.01); *A61K 33/24* (2013.01)

(58) Field of Classification Search
CPC .................................................. A61K 9/1273
See application file for complete search history.

(56) References Cited

U.S. PATENT DOCUMENTS 5,023,087 A 6/1991 Yau-Young
6,897,196 B1 5/2005 Szoka, Jr. et al.
(Continued)

FOREIGN PATENT DOCUMENTS

WO 2004/103344 A1 12/2004

OTHER PUBLICATIONS

Felnerova, et al., "Liposomes and Virosomes as Delivery Systems for Antigens, Nucleic Acids and Drugs.," Current Opinion in Biotechnology, 15, 2004, pp. 518-529.
(Continued)

*Primary Examiner* — Benjamin J Packard
(74) *Attorney, Agent, or Firm* — Mayer Brown LLP

(57) ABSTRACT

The present invention provides methods for delivery of therapeutic agents to a subject using multi-component liposomal systems. The methods include administration of a therapeutic liposome containing an active agent, followed by a administration of an attacking liposome that induces release of the agents from the therapeutic liposome.

20 Claims, 8 Drawing Sheets

Related U.S. Application Data continuation of application No. 13/664,457, filed on Oct. 31, 2012, now Pat. No. 9,370,489.

(60) Provisional application No. 61/553,786, filed on Oct. 31, 2011.

(51) Int. Cl.
*A61K 31/704* (2006.01)
*A61K 31/7068* (2006.01)
*A61K 9/00* (2006.01)

(56) References Cited

U.S. PATENT DOCUMENTS

| | | | |
|---|---|---|---|
| 7,205,273 | B2 | 4/2007 | Cullis et al. |
| 7,273,620 | B1 | 9/2007 | Zhigaltsev et al. |
| 2005/0142182 | A1 | 6/2005 | Wang et al. |
| 2007/0065798 | A1 | 3/2007 | Patz et al. |
| 2007/0248541 | A1 | 10/2007 | Tagawa et al. |
| 2008/0166403 | A1 | 7/2008 | Wang et al. |
| 2011/0020434 | A1 | 1/2011 | O'Halloran et al. |

OTHER PUBLICATIONS

Guo, et al., "Chemical Approaches to Triggerable Lipid Vesicles for Drug and Gene Delivery," Acc. Chem. Res., 2003, 36, pp. 335-341.
Guo, et al., "Steric Stabilization of Fusogenic Liposomes by a Low-pH Sensitive PEG-Diortho Ester-Lipid Conjugate," Bionconjugate Chem., 2001, 12, pp. 291-300.
Pantazatos, et al., "Directly Observed Membrane Fusion Between Oppositely Charged Phospholipid Bilayers," J. Membrane Biol., 170, 1999, pp. 27-38.
Stamatatos, et al., "Interactions of Cationic Lipid Vesicles with Negatively Charged Phospholipid Vesicles and Biological Membranes," Biochemistry, 1988, 27, pp. 3917-3925.
Weecharangsan, et al., "Disulfide-Linked Liposomes: Effective Delivery Vehicle for Bcl-2 Antisense Oligodeoxyribonucleotide G3139," Anticancer Research, 30, 2010, pp. 31-38.
Zhai, et aL, "A Liposomal Delivery Vehicle for the Anticancer Agent Gossypol," Anticancer Research 28, 2008, pp. 2801-2806.
Zhigaltsev, et al., "Triggered Release of Doxorubicin Following Mixing of Cationic and Anionic Liposomes," Biochimica at Biophysica Acta 1565, 2002, pp. 129-135.
International Search Report dated Apr. 22, 2013 corresponding to PCT/US2012/062635, 4 pages.
De La Maza, et al., "Solubilizing Effects Caused by the Nonionic Surfactant Dodecylmaltoside in Phosphatidylcholine Liposomes," Biophysical Journal, 72, Apr. 1997, pp. 1668-1675.
International Preliminary Report on Patentability (Chapter I of the Patent Cooperation Treaty) dated May 6, 2014 and aorresponding to PCT/US2012/062635, 8 pages.

A

B

A

B

A

B

COMBINATIONAL LIPOSOME COMPOSITIONS FOR CANCER THERAPY

CROSS-REFERENCES TO RELATED APPLICATIONS

This patent application is a continuation of U.S. patent application Ser. No. 15/162,072, filed on May 23, 2016, which is a continuation of U.S. patent application Ser. No. 13/664,457, filed on Oct. 31, 2012, which claims priority to U.S. Provisional Application Ser. No. 61/553,786, filed Oct. 31, 2011, which are incorporated herein by reference in their entirety to the full extent permitted by law.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Liposomes can be used as effective drug delivery vehicles, and commercially available liposomal products have been developed for treatment of diseases including cancer (Barenholz, Y., *Curr. Opin. in Colloid & Interface Sci.* 6(1): 66-77 (2001)). A liposome is a vesicle including at least one phospholipid bilayer separating an interior aqueous phase from the external aqueous environment. A liposome is capable of carrying both hydrophobic cargo in the lipid bilayer and/or hydrophilic cargo in the aqueous core. Liposome size is usually in a range from 50 to 250 nm, which is particularly suitable for targeted delivery of chemotherapy agents to solid tumor sites via the enhanced permeability and retention of cancer tissues (the EPR effect) (Maeda, H., et al., *J. Controlled Release.* 65(1-2): 271 (2000)). The preferential accumulation of drug-containing liposomes at the tumor site via EPR provides a means for localizing the drug, improving drug efficacy, and reducing drug toxicity to normal cells or tissues. For example, Doxil™, an FDA-approved liposome product containing doxorubicin, has been shown to have reduced toxicity compared with the free drug (Martin, F. J., et al., "Clinical pharmacology and antitumor efficacy of DOXIL." *Medical Applications of Liposornes.* Ed. D. D. Lasic. Amsterdam: Elsevier, 1998, pp 635-688).

However, the benefits of liposomal drug delivery vehicles are limited by drawbacks including liposome metabolism and excretion from the body, as well as a certain level of intrinsic toxicity and side effects due to systemic distribution and delivery. In particular, optimizing the release rate of liposomal drug is a difficult balancing act between in vivo half life and release. In general, leaky liposomes will make the encapsulated drug more available, but cause more risk in toxicity similar to the free drug. On the other hand, less leaky liposomes may reduce toxicity, but they may not provide the desirable drug release for efficacy as shown in a cisplatin preparation (SPI-077) (Kim, E. S. et al., *Lung Cancer.* 34(3): 427-432 (2001)). Therefore, balancing efficacy and safety in the development and administration of liposomal drug products constitutes a significant challenge.

Accordingly, there is a need to develop formulations and delivery methods which overcome the limitations of therapies based on singular liposomal preparations. The present invention addresses this and other needs, providing a means of improving drug safety and efficacy.

BRIEF SUMMARY OF THE INVENTION

In one aspect, the present invention provides a method for delivering a therapeutic agent to a subject, the method comprising:
  a) administering to the subject a liposome comprising a therapeutic agent; and
  b) administering to the subject a lipid nanoparticle comprising a triggering agent;
whereby release of the therapeutic agent from the liposome following administration of the lipid nanoparticle is increased, compared to the release of the therapeutic agent from the liposome without administration of the lipid nanoparticle.

In a second aspect, the invention provides a kit for delivering a therapeutic agent to a subject, the kit comprising:
  a) a first composition comprising a liposome containing a therapeutic agent; and
  b) a second composition comprising a lipid nanoparticle containing a non-ionic triggering agent;
wherein the first and second compositions are stored separately prior to administration to the subject.

DETAILED DESCRIPTION OF THE INVENTION

I. General

Figure 1:
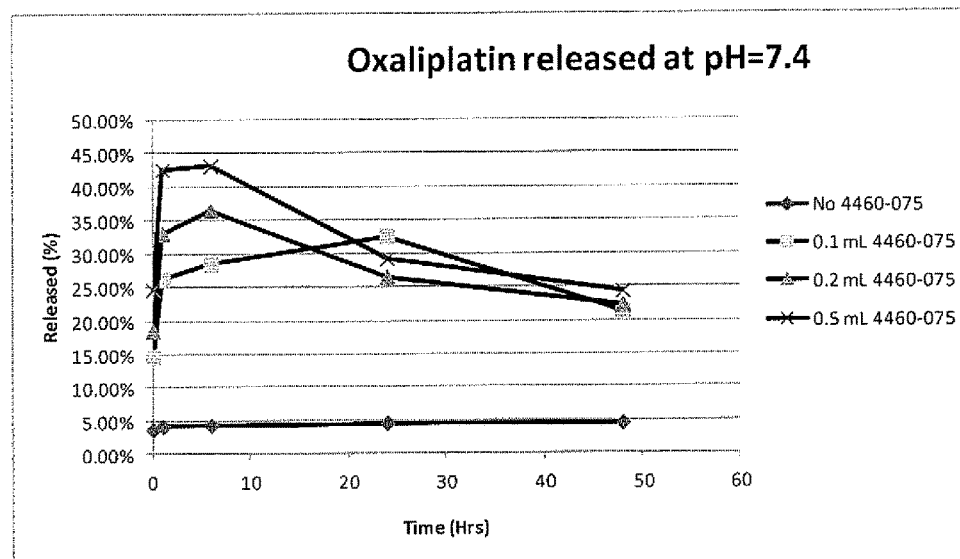
FIG. 1 shows oxaliplatin release from therapeutic liposomes triggered by attacking liposome 4460-075 at (a) pH=5.0 and (b) pH=7.4.
Figure 1:
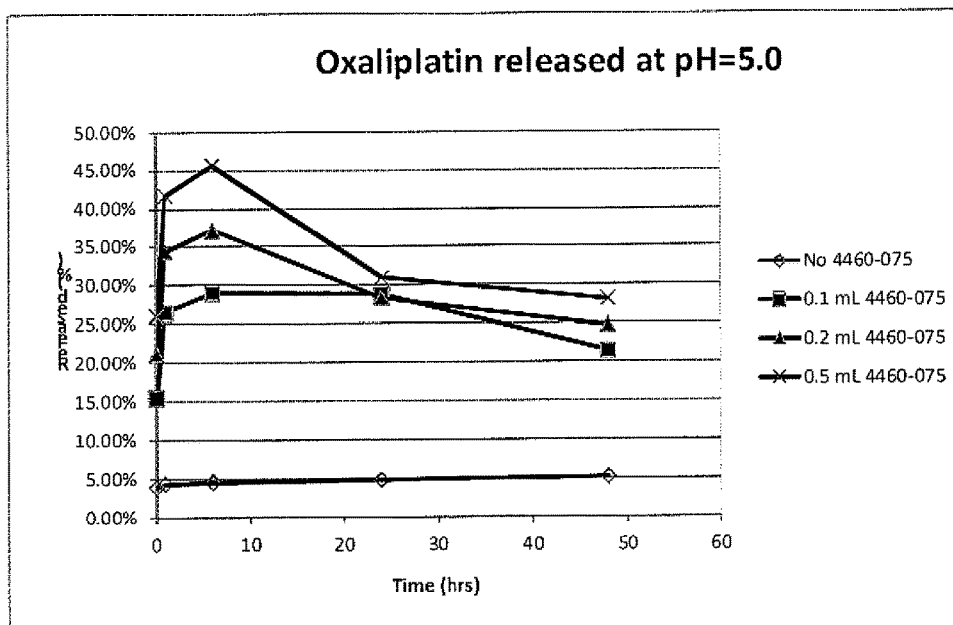

The present invention relates to the use of multiple lipid compositions for delivery of drugs or other agents to a subject. The methods of the invention include the administration of separate lipid compositions including a therapeutic liposome and an attacking agent. The therapeutic liposome is a liposomal component containing a therapeutic agent and/or other agents (e.g., diagnostic agents). The attacking agent is a lipid nanoparticle (a liposome, a micelle, or a mixture thereof) containing a triggering agent which can increase the release of cargo from the therapeutic liposome. In the present context, the terms "attacking agent" and "lipid nanoparticle containing a triggering agent" are used interchangeably. In some embodiments, the therapeutic liposome and the attacking agent are collectively referred to as a "dualsome." The two components can be stored separately, and the attacking agent can be administered following administration of the therapeutic liposome in order to effect a regulated delivery of the therapeutic liposome's cargo. The methods of the invention include two steps: 1) administration of the therapeutic liposome, and 2) administration of the attacking agent to trigger an increase in drug release from the therapeutic liposomes relative to the release in the absence of the attacking agent. The methods of the invention can prevent the early release of agents from the therapeutic liposome before it reaches a target site within a subject. The methods overcome the current dilemma of using a singular liposomal preparation for drug delivery, thus improving therapeutic efficacy and safety as well as patient compliance.

II. Definitions

As used herein, the terms "delivery" and "delivering" refer to conveyance of a therapeutic agent to a subject using the methods of the invention. Delivery may be localized to a particular location in a subject, such as a tissue, an organ, or cells of a particular type.

As used herein, the term "therapeutic agent" refers to a compound or molecule that, when present in an effective amount, produces a desired therapeutic effect on a subject in need thereof. The present invention contemplates a broad range of therapeutic agents and their use in conjunction with the liposome compositions, as further described herein.

As used herein, the term "subject" refers to any mammal, in particular a human, at any stage of life.

As used herein, the terms "administer," "administered," or "administering" refer to methods of administering the liposome compositions of the present invention. The liposome compositions of the present invention can be administered in a variety of ways, including topically, parenterally, intravenously, intradermally, intramuscularly, colonically, rectally or intraperitoneally. The liposome compositions can also be administered as part of a composition or formulation.

As used herein, the term "liposome" encompasses any compartment enclosed by a lipid bilayer. The term liposome includes unilamellar vesicles which are comprised of a single lipid bilayer and generally have a diameter in the range of about 20 to about 400 nm. Liposomes can also be multilamellar, which generally have a diameter in the range of 1 to 10 pm. In some embodiments, liposomes can include multilamellar vesicles (MLV), large unilamellar vesicles (LUV), and small unilamellar vesicles (SUV).

As used herein, the term "micelle" refers to an aggregate of amphiphilic molecules such as lipids, assembled so as to form a particle with a hydrophobic interior and a hydrophilic exterior. Micelles are generally spherical assemblies with diameters below 100 nm, although a range of micelle diameters and varying micelle shapes, such as discoid micelles, are known in the art.

As used herein, the term "non-ionic triggering agent" refers to a substance lacking charged functional groups, including anionic functional groups and cationic functional groups, which upon administration to a subject causes an increase in the release of drug cargo from the therapeutic liposome of the invention. Examples of non-ionic triggering agents include TPGS and polyoxyethylene 40 stearate.

As used herein, the term "accumulated" refers to liposomes that have amassed at a given site in a subject after administration, having ceased to systemically circulate within the subject. In some cases, the accumulation may be due to binding of a specific biomarker at the target site by a liposome comprising a ligand that recognizes the biomarker. In some cases, the liposome accumulation may be due to the enhanced permeability and retention characteristics of certain tissues such as cancer tissues. Liposome accumulation may be assessed by any suitable means, such as compartmental analysis of test subjects or non-invasive techniques such as single photon emission computer tomography (SPECT), positron emission tomography (PET) or nuclear magnetic resonance imaging (NMR/MRI). However, one of skill in the art can plan the timing of liposome administration to a particular subject so as to allow for sufficient accumulation at a target site without directly measuring accumulation in the subject.

As used herein, the term "target site" refers to a location at which liposome accumulation and delivery of an active agent is desired. In some cases, the target site can be a particular tissue or cell and may be associated with a particular disease state.

As used herein, the term "contact" refers to interaction of a first liposome with a second liposome so as to destabilize the first liposome or otherwise effect release of the encapsulated agents from the first liposome.

As used herein, the term "release" refers to the movement of an active agent in a liposome from the liposome core or lipid bilayer to the external environment.

As used herein, the term "lipid" refers to lipid molecules that can include fats, waxes, steroids, cholesterol, fat-soluble vitamins, monoglycerides, diglycerides, phospholipids, sphingolipids, glycolipids, cationic or anionic lipids, derivatized lipids, and the like, as described in detail below. Lipids can form micelles, monolayers, and bilayer membranes. The lipids can self-assemble into liposomes.

As used herein, the terms "molar percentage" and "mol %" refer to the number of a moles of a given lipid or surfactant component of a liposome divided by the total number of moles of all lipid or surfactant components. Unless explicitly stated, the amounts of active agents, diluents, or other components are not included when calculating the mol % for a lipid or surfactant component of a liposome.

As used herein, the term "kit" refers to a set of two or more components necessary for employing the methods of the invention. Kit components can include, but are not limited to, liposomes of the present invention, reagents, buffers, containers and/or equipment.

As used herein, the phrase "stored separately" refers to a manner of liposome storage that prevents a first population of liposomes from contacting another population of liposomes.

III. Embodiments of the Invention

In one aspect, the present invention provides a method for delivering a therapeutic agent to a subject. The method includes: a) administering to the subject a liposome comprising a therapeutic agent; and b) administering to the subject a lipid nanoparticle comprising a non-ionic triggering agent; whereby release of the therapeutic agent from the liposome after administration of the triggering agent is increased as compared to the release of the therapeutic agent from the liposome without administration of the triggering agent. The liposome comprising a therapeutic agent is referred to as a "therapeutic liposome."

The liposomes of the present invention comprise an aqueous compartment enclosed by at least one lipid bilayer. When lipids that include a hydrophilic headgroup are dispersed in water they can spontaneously form bilayer membranes referred to as lamellae. The lamellae are composed of two monolayer sheets of lipid molecules with their non-polar (hydrophobic) surfaces facing each other and their polar (hydrophilic) surfaces facing the aqueous medium. The term liposome includes unilamellar vesicles which are comprised of a single lipid bilayer and generally have a diameter in the range of about 20 to about 400 nm, about 50 to about 300 nm, or about 100 to 200 nm. Liposomes can also be multilamellar, which generally have a diameter in the range of 1 to 10 μm with anywhere from two to hundreds of concentric lipid bilayers alternating with layers of an aqueous phase. In some embodiments, liposomes can include multilamellar vesicles (MLV), large unilamellar vesicles (LUV), and small unilamellar vesicles (SUV). The lipids of the liposome can be cationic, zwitterionic, neutral or anionic, or any mixture thereof.

The lipid nanoparticle constitutes the "attacking agent" in the methods of the present invention. In some embodiments, the lipid nanoparticle is selected from a liposome, a micelle, or mixtures thereof. The nanoparticle contains a non-ionic triggering agent, which can be a non-ionic surfactant. Examples of non-surfactants suitable for use in the methods of the invention include, but are not limited to, an ethoxylated alkylphenol, an ethoxylated fatty ester, a sorbitan derivative, a tocopherol derivative, and the like.

Administration of the attacking agent to a subject can occur at any time sufficient to increase the release of the therapeutic agent from the therapeutic liposome. In some embodiments, the attacking agent is administered to the subject after administration of the therapeutic liposome. Administration of the attacking agent can occur, for example, a few minutes or several hours after administration of the therapeutic liposome. In some embodiments, the attacking agent is administered to the subject after the therapeutic liposome has accumulated at a desired target site within the subject (typically within about 72 hours after administration). Liposome accumulation at a target site may be assessed by any suitable means, such as compartmental analysis of test subjects or non-invasive techniques such as single photon emission computer tomography (SPECT), positron emission tomography (PET) or nuclear magnetic resonance imaging (NMR/MRI). Diagnostic agents as described below, for example, may be chosen for incorporation in the therapeutic liposomes for assessment of liposome accumulation. However, one of skill in the art will appreciate that administration to a particular subject can be timed so as to allow for sufficient accumulation of therapeutic liposomes at a target site without directly measuring accumulation in the subject.

In some embodiments, release of the therapeutic agent is induced upon contact of the therapeutic liposome by the attacking agent. The amount of therapeutic agent released from the liposome can increase by any amount with administration of the attacking agent as compared to in the absence of the attacking agent. In some embodiments, administration of the attacking agent causes at least a 3-fold increase in release of the therapeutic agent from the liposome, as compared to administration of the liposome without the attacking agent. In some embodiments, administration of the attacking agent causes at least a 10-fold increase in release of the therapeutic agent from the liposome, as compared to administration of the liposome without the attacking agent. In some embodiments, administration of the attacking agent causes at least a 25-fold increase in release of the therapeutic agent from the liposome, as compared to administration of the liposome without the attacking agent.

In the present invention, the subject can be any mammal. In some embodiments, the subject is human. In some embodiments, the liposome and the lipid nanoparticle are delivered by intraperitoneal injection. One of skill in the art will appreciate that other modes of administration may be useful in the present invention.

Liposomes and Lipid Nanoparticles

The liposomes and lipid nanoparticles of the present invention can contain any suitable lipid, including cationic lipids, zwitterionic lipids, neutral lipids, or anionic lipids as described above. Suitable lipids can include fats, waxes, steroids, cholesterol, fat-soluble vitamins, monoglycerides, diglycerides, phospholipids, sphingolipids, glycolipids, cationic or anionic lipids, derivatized lipids, and the like.

Suitable phospholipids include but are not limited to phosphatidylcholine (PC), phosphatidic acid (PA), phosphatidylethanolamine (PE), phosphatidylglycerol (PG), phosphatidylserine (PS), and phosphatidylinositol (P1), dimyristoyl phosphatidyl choline (DMPC), distearoyl phosphatidyl choline (DSPC), dioleoyl phosphatidyl choline (DOPC), dipalmitoyl phosphatidyl choline (DPPC), dimyristoyl phosphatidyl glycerol (DMPG), distearoyl phosphatidyl glycerol (DSPG), dioleoyl phosphatidyl glycerol (DOPG), dipalmitoyl phosphatidyl glycerol (DPPG), dimyristoyl phosphatidyl serine (DMPS), distearoyl phosphatidyl serine (DSPS), dioleoyl phosphatidyl serine (DOPS), dipalmitoyl phosphatidyl serine (DPPS), dioleoyl phosphatidyl ethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), 1,2-dielaidoyl-sn-glycero-3-phophoethanolamine (transDOPE), and cardiolipin. Lipid extracts, such as egg PC, heart extract, brain extract, liver extract, and soy PC, are also useful in the present invention. In some embodiments, soy PC can include Hydro Soy PC (HSPC). In certain embodiments, the lipids can include derivatized lipids, such as PEGylated lipids. Derivatized lipids can include, for example, DSPE-PEG2000, cholesterol-PEG2000, DSPE-polyglycerol, or other derivatives generally known in the art.

Liposomes and lipid nanoparticles of the present invention may contain steroids, characterized by the presence of a fused, tetracyclic gonane ring system. Examples of steroids include, but are not limited to, cholesterol, cholic acid, progesterone, cortisone, aldosterone, estradiol, testosterone, dehydroepiandrosterone. Synthetic steroids and derivatives thereof are also contemplated for use in the present invention.

Cationic lipids contain positively charged functional groups under physiological conditions. Cationic lipids include, but are not limited to, N,N-dioleyl-N,N-dimethylammonium chloride (DODAC), N,N-distearyl-N,N-dimethylammonium bromide (DDA13), N-(1-(2,3-dioleoyloxy)propyl)-N,N,N-trimethylammonium chloride (DOTAP), N-(1-(2,3-dioleoyloxy)propyl)-N,N,N-trimethylammonium chloride (DOTMA), N-[1-(2,3-ditetradecyloxy)propyl]-N,N-dimethyl-N-hydroxyethylammonium bromide (DMRIE), N-[1-(2,3,dioleyloxy)propyl]-N,N-dimethyl-N-hydroxy ethylammonium bromide (DORIE), 3B—[N—(N',N'-dimethylaminoethane) carbamoyl]cholesterol (DC-Chol), dimethyldioctadecylammonium (DDAB) and N,N-dimethyl-2,3-dioleyloxy)propylamine (DODMA).

In some embodiments, the therapeutic liposome includes one or more lipids which can be a phospholipid, a steroid, and/or a cationic lipid. In some embodiments, the phospholipid is a phosphatidylcholine, a phosphatidylglycerol, a phosphatidylethanolamine, a phosphatidylserine, a phosphatidylinositol, or a phosphatidic acid. In some embodiments, the phosphatidylcholine is DSPC. In some embodiments, the phosphatidylglycerol is DSPG. In some embodiments, the phosphatidylethanolamine is DSPE-PEG(2000). In some embodiments, the steroid is cholesterol.

As described above, the lipid nanoparticle constituting the "attacking agent" is selected from the group of consisting of a second liposome, a micelle, or mixtures thereof. In some embodiments, the lipid nanoparticle is a second liposome. The second liposome is referred to as an "attacking liposome." In some embodiments, the attacking liposome comprises one or more lipids selected from the group consisting of a phospholipid, a steroid, and a cationic lipid. In some embodiments, the phospholipid is a phosphatidylcholine, a phosphatidylglycerol, a phosphatidylethanolamine, a phosphatidylserine, a phosphatidylinositol, or a phosphatidic acid. In some embodiments, the phosphatidylcholine is DPPC. In some embodiments, the steroid is cholesterol. In some embodiments, the cationic lipid is DOTAP. In some embodiments, the non-ionic triggering agent is TPGS.

Any suitable combination of lipids can be used to provide the liposomes and lipid nanoparticles of the invention. The lipid compositions can be tailored to affect characteristics such as leakage rates, stability, particle size, zeta potential, protein binding, in vivo circulation, and/or accumulation in tissues or organs. For example, DSPC and/or cholesterol can be used to decrease leakage from liposomes. Negatively or positively lipids, such as DSPG and/or DOTAP, can be included to affect the surface charge of a liposome or lipid nanoparticle. In some embodiments, the lipid compositions can include about ten or fewer types of lipids, or about five or fewer types of lipids, or about three or fewer types of lipids. In some embodiments, the molar percentage (mol %) of a specific type of lipid present typically comprises from about 0% to about 10%, from about 10% to about 30%, from about 30% to about 50%, from about 50% to about 70%, from about 70% to about 90%, from about 90% to 100% of the total lipid present in a liposome or lipid nanoparticle. In some embodiments, the therapeutic liposome comprises 40-80 mol % DSPC, 5-50 mol % cholesterol, 0-30 mol % DSPG, and 0-10 mol % DSPE-PEG(2000). In some embodiments, the attacking liposome comprises 40-70 mol % DPPC, 5-20 mol % cholesterol, 0-20 mol % DOTAP, and 20-40 mol % TPGS.

The lipid nanoparticles of the invention can contain surfactants including non-ionic surfactants, some of which can act as triggering agents to facilitate release of the therapeutic liposome's cargo. Examples of non-ionic surfactants include, but are not limited to, ethoxylated alkylphenols, ethoxylated fatty esters, sorbitan derivatives, and tocopherol derivatives. Surfactants contemplated for use in the present invention include D-α-tocopherol polyethylene glycol succinate (TPGS), which is available having different polyethylene glycol sizes. In some embodiments, the molecular weight range for polyethylene glycol in TPGS is 400-5000. In still other embodiments, the molecular weight range for polyethylene glycol in TPGS is 800-2000. In yet other embodiments, the molecular weight range for polyethylene glycol in TPGS is 800-1500. One particularly useful TPGS is TPGS(1000), in which to total molecular weight of the D-α-tocopherol polyethylene glycol succinate is about 1543. As used herein, the term "TPGS" refers to TPGS(1000) unless a different size/weight is provided. Other useful non-ionic surfactants include: polyethylene glycol p-(1,1,3,3-tetramethylbutyl)-phenyl ether, polyoxyethylene (2) isooctylphenyl ether, polyoxyethylene (150) dinonylphenyl ether, dodecanoic acid 2,3-dihydroxypropyl ester, polyoxyethylene (20) sorbitan monolaurate, polyoxyethylene (20) sorbitan monopalmitate, polyoxyethylene (20) sorbitan monostearate, polyoxyethylene (20) sorbitan monooleate, and the like.

One of skill in art will recognize that the lipid compositions may be adjusted to modulate the release properties or other characteristics of the liposomes as required by a given application.

Therapeutic Agents

The therapeutic liposomes of the present invention comprise one or more therapeutic agents present anywhere in, on, or around the nanocarrier. For example, a therapeutic agent be embedded in the lipid bilayer of the liposome, encapsulated in the aqueous core of the liposome, or tethered to the exterior of the liposome. The therapeutic agent or agents used in the present invention can include any agent directed to treat a condition in a subject. In general, any therapeutic agent known in the art can be used, including without limitation agents listed in the United States Pharmacopeia (U.S.P.), *Goodman and Gilman's The Pharmacological Basis of Therapeutics*, 10$^{th}$ Ed., McGraw Hill, 2001; Katzung, Ed., *Basic and Clinical Pharmacology*, McGraw-Hill/Appleton & Lange, 8$^{th}$ ed., Sep. 21, 2000; *Physician's Desk Reference* (Thomson Publishing; and/or *The Merck Manual of Diagnosis and Therapy*, 18$^{th}$ ed., 2006, Beers and Berkow, Eds., Merck Publishing Group; or, in the case of animals, *The Merck Veterinary Manual*, 9th ed., Kahn Ed., *Merck Publishing Group*, 2005; all of which are incorporated herein by reference.

Therapeutic agents can be selected depending on the type of disease desired to be treated. For example, certain types of cancers or tumors, such as carcinoma, sarcoma, leukemia, lymphoma, myeloma, and central nervous system cancers as well as solid tumors and mixed tumors, can involve administration of the same or possibly different therapeutic agents. In certain embodiments, a therapeutic agent can be delivered to treat or affect a cancerous condition in a subject and can include chemotherapeutic agents, such as alkylating agents, antimetabolites, anthracyclines, alkaloids, topoisomerase inhibitors, and other anticancer agents. In some embodiments, the agents can include antisense agents, microRNA, siRNA and/or shRNA agents.

Therapeutic agents can include an anticancer agent or cytotoxic agent including but not limited to avastin, doxorubicin, cisplatin, oxaliplatin, carboplatin, 5-fluorouracil, gemcitibine or taxanes, such as paclitaxel and docetaxel. Additional anti-cancer agents can include but are not limited to 20-epi-1,25 dihydroxyvitamin D3,4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethhnide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, eactinomycin, caleipotriol, calphostin C, calusterone, camptothecin derivatives, canarypox IL-2, capecitabine, caracemide, carbetimer, carboplatin, carboxamide-amino-triazole, carboxyamidotriazole, carest M3, carmustine, cam 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cisporphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, daclizimab, dactinomyein, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarrnycin SA, ebselen, ecomustine, edatrexate, edelfosine, edrecolomab, eflomithine, eflomithine hydrochloride, elemene, elsamitrucin, emitefur, enloplatin, enpromate, epipropidine, epirubicin, epirubicin hydrochloride, episteride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, fonnestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohornohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, 06-benzylguanine, octreotide, okicenone, oligonucleotides, onapristone, ondansetron, oracin, oral cytokine inducer, orinaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride.

In some embodiments, the therapeutic agents can be part of cocktail of agents that includes administering two or more therapeutic agents. For example, a liposome having both cisplatin and oxaliplatin can be administered. In addition, the therapeutic agents can be delivered before, after, or with immune stimulatory adjuvants, such as aluminum gel or salt adjuvants (e.g., aluminum phosphate or aluminum hydroxide), calcium phosphate, endotoxins, toll-like receptor adjuvants and the like.

Therapeutic agents of the present invention can also include radionuclides for use in therapeutic applications. For example, emitters of Auger electrons, such as $^{111}$In, can be combined with a chelate, such as diethylenetriaminepentaacetic acid (DTPA) or 1,4,7,10-tetraazacyclododecane-1,4,7,10-tetraacetic acid (DOTA), and included in a liposome to be used for treatment. Other suitable radionuclide and/or radionuclide-chelate combinations can include but are not limited to beta radionuclides ($^{177}$Lu, $^{153}$Sm, $^{88/90}$Y) with DOTA, $^{64}$Cu-TETA, $^{188/186}$Re(CO)$_3$-IDA; $^{188/186}$Re(CO)triamines (cyclic or linear), $^{188/186}$Re(CO)$_3$-Enpy2, and $^{188/186}$Re(CO)$_3$-DTPA.

In some embodiments of the present invention, the therapeutic agent can be cisplatin, oxaliplatin, carboplatin, gemcitabine, 5-fluorouracil, doxorubicin, and a taxane. In some embodiments, the therapeutic agent is cisplatin or oxaliplatin.

Loading of the therapeutic agents can be carried out through a variety of ways known in the art, as disclosed for example in the following references: de Villiers, M. M. et al., Eds., *Nanotechnology in Drug Delivery*, Springer (2009); Gregoriadis, G., Ed., *Liposome Technology: Entrapment of drugs and other materials into liposomes*, CRC Press (2006). In some embodiments, one or more therapeutic agents can be loaded into liposomes. Loading of liposomes can be carried out, for example, in an active or passive manner. For example, a therapeutic agent can be included during the self-assembly process of the liposomes in a solution, such that the therapeutic agent is encapsulated within the liposome. In certain embodiments, the therapeutic agent may also be embedded in the liposome bilayer or within multiple layers of multilamellar liposome. In alternative embodiments, the therapeutic agent can be actively loaded into liposomes. For example, the liposomes can be exposed to conditions, such as electroporation, in which the bilayer membrane is made permeable to a solution containing therapeutic agent thereby allowing for the therapeutic agent to enter into the internal volume of the liposomes.

Diagnostic Agents

The therapeutic liposomes of the present invention may also contain diagnostic agents. A diagnostic agent used in the present invention can include any diagnostic agent known in the art, as provided, for example, in the following references: Armstrong et al., *Diagnostic Imaging*, 5$^{th}$ Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). A diagnostic agent can be detected by a variety of ways, including as an agent providing and/or enhancing a detectable signal that includes, but is not limited to, gamma-emitting, radioactive, echogenic, optical, fluorescent, absorptive, magnetic or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like.

In some embodiments, a diagnostic agent can include chelators that bind to metal ions to be used for a variety of diagnostic imaging techniques. Exemplary chelators include but are not limited to ethylenediaminetetraacetic acid (EDTA), [4-(1,4,8,11-tetraazacyclotetradec-1-yl) methyl] benzoic acid (CPTA), cyclohexanediaminetetraacetic acid (CDTA), ethylenebis(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7,10-tetraazacyclododecane-1,4,7,10-tetra (methylene phosphonic acid) (DOTP), 1,4,8,11-tetraazacyclododecane-1,4,8,11-tetraacetic acid (TETA), 1,4,7,10-tetraazacyclododecane-1,4,7,10-tetraacetic acid (DOTA), and derivatives thereof.

A radioisotope can be incorporated into some of the diagnostic agents described herein and can include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{123}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In other embodiments, the agents can include DOTA and its various analogs with $^{111}$In, $^{177}$Lu, $^{153}$Sm, $^{88/90}$Y $^{62/64/67}$Cu, or $^{67/68}$Ga. In some embodiments, the liposomes can be radiolabeled, for example, by incorporation of lipids attached to chelates, such as DTPA-lipid, as provided in the following references: Phillips et al., *Wiley Interdisciplinary Reviews: Nanomedicine and Nanobiotechnology*, 1(1): 69-83 (2008); Torchilin, V. P. & Weissig, V., Eds. *Liposomes 2nd Ed*: Oxford Univ. Press (2003); Elbayoumi, T. A. & Torchilin, V. P., *Eur. J. Nucl. Med. Mol. Imaging* 33:1196-1205 (2006); Mougin-Degraef, M. et al., *Int'l J. Pharmaceutics* 344:110-117 (2007).

In other embodiments, the diagnostic agents can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives having the general structure of 4,4-difluoro-4-bora-3a,4a-diaza-s-indacene, and/or conjugates and/or derivatives of any of these. Other agents that can be used include, but are not limited to, for example, fluorescein, fluorescein-polyaspartic acid conjugates, fluorescein-polyglutamic acid conjugates, fluorescein-polyarginine conjugates, indocyanine green, indocyanine-dodecaaspartic acid conjugates, indocyanine-polyaspartic acid conjugates, isosulfan blue, indole disulfonates, benzoindole disulfonate, bis(ethylcarboxymethyl)indocyanine, bis(pentylcarboxymethyl)indocyanine, polyhydroxyindole sulfonates, polyhydroxybenzoindole sulfonate, rigid heteroatomic indole sulfonate, indocyaninebispropanoic acid, indocyaninebishexanoic acid, 3,6-dicyano-2,5-[(N,N,N',N'-tetrakis(carboxymethyl)amino]pyrazine, 3,6-[(N,N,N',N'-tetrakis(2-hydroxyethyl)amino]pyrazine-2,5-dicarboxylic acid, 3,6-bis(N-azatedino)pyrazine-2,5-dicarboxylic acid, 3,6-bis(N-morpholino)pyrazine-2,5-dicarboxylic acid, 3,6-bis(N-piperazino)pyrazine-2,5-dicarboxylic acid, 3,6-bis(N-thiomorpholino)pyrazine-2,5-dicarboxylic acid, 3,6-bis(N-thiomorpholino)pyrazine-2,5-dicarboxylic acid S-oxide, 2,5-dicyano-3,6-bis(N-thiomorpholino)pyrazine S,S-dioxide, indocarbocyaninetetrasulfonate, chloroindocarbocyanine, and 3,6-diaminopyrazine-2,5-dicarboxylic acid.

One of ordinary skill in the art will appreciate that particular optical agents used can depend on the wavelength used for excitation, depth underneath skin tissue, and other factors generally well known in the art. For example, optimal absorption or excitation maxima for the optical agents can vary depending on the agent employed, but in general, the optical agents of the present invention will absorb or be excited by light in the ultraviolet (UV), visible, or infrared (IR) range of the electromagnetic spectrum. For imaging, dyes that absorb and emit in the near-IR (~700-900 nm, e.g., indocyanines) are preferred. For topical visualization using an endoscopic method, any dyes absorbing in the visible range are suitable.

In some embodiments, the non-ionizing radiation employed in the process of the present invention can range in wavelength from about 350 nm to about 1200 nm. In one exemplary embodiment, the fluorescent agent can be excited by light having a wavelength in the blue range of the visible portion of the electromagnetic spectrum (from about 430 nm to about 500 nm) and emits at a wavelength in the green range of the visible portion of the electromagnetic spectrum (from about 520 nm to about 565 nm). For example, fluorescein dyes can be excited with light with a wavelength of about 488 nm and have an emission wavelength of about 520 nm. As another example, 3,6-diaminopyrazine-2,5-dicarboxylic acid can be excited with light having a wavelength of about 470 nm and fluoresces at a wavelength of about 532 nm. In another embodiment, the excitation and emission wavelengths of the optical agent may fall in the near-infrared range of the electromagnetic spectrum. For example, indocyanine dyes, such as indocyanine green, can be excited with light with a wavelength of about 780 nm and have an emission wavelength of about 830 nm.

In yet other embodiments, the diagnostic agents can include but are not limited to magnetic resonance (MR) and x-ray contrast agents that are generally well known in the art, including, for example, iodine-based x-ray contrast agents, superparamagnetic iron oxide (SPIO), complexes of gadolinium or manganese, and the like. (See, e.g., Armstrong et al., *Diagnostic Imaging*, 5$^{th}$ Ed., Blackwell Publishing (2004)). In some embodiments, a diagnostic agent can include a magnetic resonance (MR) imaging agent. Exemplary magnetic resonance agents include but are not limited to paramagnetic agents, superparamagnetic agents, and the like. Exemplary paramagnetic agents can include but are not limited to gadopentetic acid, gadoteric acid, gadodiamide, gadolinium, gadoteridol mangafodipir, gadoversetamide, ferric ammonium citrate, gadobenic acid, gadobutrol, or gadoxetic acid. Superparamagnetic agents can include but are not limited to superparamagnetic iron oxide and ferristene. In certain embodiments, the diagnostic agents can include x-ray contrast agents as provided, for example, in the following references: H. S Thomsen, R. N. Muller and R. F. Mattrey, Eds., *Trends in Contrast Media*, (Berlin: Springer-Verlag, 1999); P. Dawson, D. Cosgrove and R. Grainger, Eds., *Textbook of Contrast Media* (ISIS Medical Media 1999); Torchilin, V. P., *Curr. Pharm. Biotech.* 1:183-215 (2000); Bogdanov, A. A. et al., *Adv. Drug Del. Rev.* 37:279-293 (1999); Sachse, A. et al., *Investigative Radiology* 32(1):44-50 (1997). Examples of x-ray contrast agents include, without limitation, iopamidol, iomeprol, iohexol, iopentol, iopromide, iosimide, ioversol, iotrolan, iotasul, iodixanol, iodecimol, ioglucamide, ioglunide, iogulamide, iosarcol, ioxilan, iopamiron, metrizamide, iobitridol and iosimenol. In certain embodiments, the x-ray contrast agents can include iopamidol, iomeprol, iopromide, iohexol, iopentol, ioversol, iobitridol, iodixanol, iotrolan and iosimenol.

As for the therapeutic agents described above, the diagnostic agents can be associated with the therapeutic liposome in a variety of ways, including for example being embedded or encapsulated in the liposome. Similarly, loading of the diagnostic agents can be carried out through a variety of ways known in the art, as disclosed for example in the following references: de Villiers, M. M. et al., Eds., *Nanotechnology in Drug Delivery*, Springer (2009); Gregoriadis, G., Ed., *Liposome Technology: Entrapment of drugs and other materials into liposomes*, CRC Press (2006).

Formulation and Administration

In some embodiments, the present invention can include a liposome composition and a physiologically (i.e., pharmaceutically) acceptable carrier. As used herein, the term "carrier" refers to a typically inert substance used as a diluent or vehicle for a drug such as a therapeutic agent. The term also encompasses a typically inert substance that imparts cohesive qualities to the composition. Typically, the physiologically acceptable carriers are present in liquid form. Examples of liquid carriers include physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Since physiologically acceptable carriers are determined in part by the particular composition being administered as well as by the particular method used to administer the composition, there are a wide variety of suitable formulations of pharmaceutical compositions of the present invention (See, e.g., Remington's Pharmaceutical Sciences, $17^{th}$ ed., 1989).

The compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate. Sugars can also be included for stabilizing the compositions, such as a stabilizer for lyophilized liposome compositions.

The liposome composition of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which includes an effective amount of a packaged liposome composition with a suppository base. Suitable suppository bases include natural or synthetic triglycerides or paraffin hydrocarbons. In addition, it is also possible to use gelatin rectal capsules which contain a combination of the liposome composition of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, topically, intraperitoneally, intravesically, or intrathecally. Parenteral administration and intravenous administration are the preferred methods of administration. The formulations of liposome compositions can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., a liposome composition. The unit dosage form can be a packaged preparation, the package containing discrete quantities of preparation. The composition can, if desired, also contain other compatible therapeutic agents.

In therapeutic use for the treatment of cancer, the liposome compositions including a therapeutic and/or diagnostic agent utilized in the pharmaceutical compositions of the present invention can be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the liposome composition being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a particular liposome composition in a particular patient. Determination of the proper dosage for a particular situation is within the skill of the practitioner. Generally, treatment is initiated with smaller dosages which are less than the optimum dose of the liposome composition. Thereafter, the dosage is increased by small increments until the optimum effect under circumstances is reached. For convenience, the total daily dosage may be divided and administered in portions during the day, if desired.

Targeting Agents

In some cases, liposome accumulation at a target site may be due to the enhanced permeability and retention characteristics of certain tissues such as cancer tissues. Accumulation in such a manner often results in part because of liposome size and may not require special targeting functionality. In other cases, the liposomes of the present invention can also include a targeting agent. Generally, the targeting agents of the present invention can associate with any target of interest, such as a target associated with an organ, tissues, cell, extracellular matrix, or intracellular region. In certain embodiments, a target can be associated with a particular disease state, such as a cancerous condition. In some embodiments, the targeting component can be specific to only one target, such as a receptor. Suitable targets can include but are not limited to a nucleic acid, such as a DNA, RNA, or modified derivatives thereof. Suitable targets can also include but are not limited to a protein, such as an extracellular protein, a receptor, a cell surface receptor, a tumor-marker, a transmembrane protein, an enzyme, or an antibody. Suitable targets can include a carbohydrate, such as a monosaccharide, disaccharide, or polysaccharide that can be, for example, present on the surface of a cell.

In certain embodiments, a targeting agent can include a target ligand (e.g., an RGD-containing peptide), a small molecule mimic of a target ligand (e.g., a peptide mimetic ligand), or an antibody or antibody fragment specific for a particular target. In some embodiments, a targeting agent can further include folic acid derivatives, B-12 derivatives, integrin RGD peptides, NGR derivatives, somatostatin derivatives or peptides that bind to the somatostatin receptor, e.g., octreotide and octreotate, and the like. The targeting agents of the present invention can also include an aptamer. Aptamers can be designed to associate with or bind to a target of interest. Aptamers can be comprised of, for example, DNA, RNA, and/or peptides, and certain aspects of aptamers are well known in the art. (See. e.g., Klussman, S., Ed., The Aptamer Handbook, Wiley-VCH (2006); Nissenbaum, E. T., *Trends in Biotech*. 26(8): 442-449 (2008)).

Kits for Administration of Active Agents

In another aspect, the present invention also provides kits for administering the liposomes and lipid nanoparticles to a subject for treating a disease state. In some embodiments, the invention provides a kit for delivering a therapeutic agent to a subject, the kit comprising: a) a first composition comprising a liposome containing a therapeutic agent; and b) a second composition comprising a lipid nanoparticle containing a non-ionic triggering agent; wherein the first and second compositions are stored separately prior to administration to the subject.

Such kits typically include two or more components necessary for treating a disease state, such as a cancerous condition. Components can include the lipid compositions of the present invention, reagents, buffers, containers and/or equipment. The liposomes and lipid nanoparticles can be in lyophilized form and then reconstituted prior to administration. In certain embodiments, the kits of the present invention can include packaging assemblies that can include one or more components used for treating the disease state of a patient. For example, a packaging assembly may include separate containers that house the therapeutic liposomes and attacking agents as described herein. A separate container may include other excipients or agents that can be mixed with the compositions prior to administration to a patient. In some embodiments, a physician may select and match certain components and/or packaging assemblies depending on the treatment or diagnosis needed for a particular patient.

IV. Examples

The practice of this invention is illustrated with, but not intended to be limited by, the examples in Table A. Through these examples, it is clearly demonstrated in vitro that the attacking liposome can be used to trigger the release of cargo from therapeutic liposomes with otherwise poor release characteristics. In examples 1, 2 and 11-12, the therapeutic liposomes contain cytotoxic agents including cisplatin or oxaliplatin. In Examples 3-10, 5-carboxyfluorescein (5-CF) is used as a marker in therapeutic liposome compositions. The characteristics of these samples are summarized in Table A below. Examples 1-5 and 10 show that the same attacking liposome (Part B) is used for triggering and/or enhancing the release of a variety of therapeutic liposome compositions (Part A) with or without stealth functionality. Examples 6-9 show the critical role of the triggering agent in the attacking liposome. The surface charge of the attacking liposome is essentially neutral in Examples 8 and 9.

TABLE A

Examples of Therapeutic and Attacking Liposomes

| Example | Encapsulated Cargo | Therapeutic Liposome Part A | Attacking Liposome Part B |
|---|---|---|---|
| 1 | Oxaliplatin | NLI COV003 F-02 - Non-stealth DSPC/DSPG/Chol (70/20/10) | 4460-075 - charged(+)/TPGS DPPC/Chol/TPGS/DOTAP (42/10/32/16) |
| 2 | Cisplatin | NLI COV00AR-02 - Non-stealth DSPC/DSPG/Chol (70/20/10) | 4460-075 - charged(+)/TPGS |
| 3 | 5-CF | 4460-090 - Non-stealth DSPC/DSPG/Chol (48/12/40) | 4460-075 - charged(+)/TPGS |
| 4 | 5-CF | 4460-077 - Non-stealth DSPC/DSPG/Chol (70/20/10) | 4460-075 - charged(+)/TPGS |
| 5 | 5-CF | 4386-143 - Stealth DSPC/Chol/DSPE-PEG(2000) (55/40/5) | 4460-075 - charged(+)/TPGS |
| 6 | 5-CF | 4460-090 - Non-stealth | 4460-084 - charged (+) DPPC/Chol/DOTAP (73/11/16) |
| 7 | 5-CF | 4460-077 - Non-stealth | 4460-084 - charged (+) |
| 8 | 5-CF | 4460-090 - Non-stealth | 4384-086 - charge(0)/TPGS DPPC/Chol/TPGS (60/10/30) |
| 9 | 5-CF | 4460-077 - Non-stealth | 4384-086 - charge(0)/TPGS |
| 10 | 5-CF | 4460-090 - Non-stealth | 4460-075 - charged(+)/TPGS |
| 11 | Oxaliplatin | NH COV003F-02 - Non-stealth | 4460-104 - charged(+)/TPGS DPPC/Chol/TPGS/DOTAP (42/10/32/16) |
| 12 | Cisplatin | NLI 4481101 - Stealth HSPC/Chol/DSPE-PEG(2000) (55/40/5) | 4460-104 - charged(+)/TPGS |

Example 1

The compositions of a therapeutic liposome (NLICOV003F-02) containing oxaliplatin and an attacking liposome (4460-075 DPPC/Chol/DOTAP/TPGS) are shown in Table 1. The therapeutic liposome (Northern Lipid Inc.)

contained 2.9 mg/mL of oxaliplatin and 71.8 mg/mL of total lipids. The attacking liposome was prepared by the following steps:

1. All lipids were weighed and placed in a round bottom flask.
2. 3:1 (v/v) chloroform/methanol was added to the flask to dissolve all lipids; the lipid concentration was about 2.5 wt %.
3. Solvents were removed from the lipid mixture using a rotoevaporator at 40° C., and vacuum was applied via the rotoevaporator for 0.5 hrs at 40° C. to remove residual solvents.
4. Drying was continued under house vacuum overnight at room temperature to remove the trace solvents.
5. Phosphate buffer saline (PBS) 1× solution (0.0067 M) was added to the dried lipid film around the bottom of the flask, and the dispersion was agitated at 70° C. for one hour.
6. The lipid dispersion (multi-lamellar vesicle dispersion) was extruded 5 times through a double packed 200 nm polycarbonate film at 70° C. in a 10-mL extruder under a pressure of ~200 psi.
7. Extrusion was continued 10 times through a double packed 100 nm polycarbonate film at 70° C. under a pressure of ~300 psi.
8. The extruded liposome sample was collected and particle size and zeta potential were measured using a Malvern Zetasizer Nano ZS.

The release of oxaliplatin in vitro from NLICOV003F-02 was conducted in PBS 1× (pH=7.4 and 5.0) solutions by admixing an aliquot of attacking liposome with the therapeutic liposome. The first sample was immediately collected (within less than 3 min) at room temperature and prepared for measuring the oxaliplatin release. The release was determined by filtering the samples through Amicon 50K MWCO centrifugal filters at 16500 rpm for 5 minutes. The released oxaliplatin in the liposome-free aqueous phase was analyzed by ICP-OES. After taking the immediate sample, the mixture was subsequently incubated at 37° C. for 48 hours. Samples were collected subsequently at 1, 6, 24 and 48 hours for analysis of oxaliplatin release. The results are shown in Table 1 and 2. The data shown in Table 2 and plotted in FIG. 1 indicate the total release of therapeutic liposome (NLICOV003F-02) was increased from ~5% at time zero to ~40% in 6-hrs by the addition of an equal amount of attacking liposome (4460-075). The results also indicate that the total release of therapeutic liposome contents increases with the amount of attacking liposome at both pH conditions. The therapeutic liposome is a non-stealth charged liposome containing 10 mol % cholesterol. The attacking liposome is oppositely charged and contains 32 mol % TPGS.

TABLE 1

Dualsome Components

| Dualsome | Name | Composition (mol %) | Particle Size (volume nm) | Zeta potential (mV) |
|---|---|---|---|---|
| Therapeutic liposome | NLICOV003F-02 | DSPC/DSPG/Chol = 70/20/10 | 83.6 | −22.6 |
| Attacking liposome | 4460-075 | DPPC/Chol/TPGS/DOTAP = 42/10/32/16 | 80.3 | 11.4 |

TABLE 2

In-vitro release of Dualsome in PBS 1X (pH = 7.4 and pH = 5.01)

| Therapeutic Liposome (NLICOV003F-02) Amount (mL) | Attacking Liposome (4460-075) Amount (mL) | PBS 1X (01 = 7.4) Added (mL) | Encapsulated Therapeutics | Immediate Release after mixing | Release at 1 hour | Release at 6 hour | Release at 24 hour | Release at 48 hour |
|---|---|---|---|---|---|---|---|---|
| 0.5 | 0.0 | 4.5 | Oxaliplatin | 3.74% | 4.17% | 4.32% | 4.58% | 4.53% |
| 0.5 | 0.1 | 4.4 | Oxaliplatin | 14.76% | 26.17% | 28.46% | 32.52% | 21.38% |
| 0.5 | 0.2 | 4.3 | Oxaliplatin | 18.61% | 33.07% | 36.55% | 26.48% | 22.33% |
| 0.5 | 0.5 | 4.0 | Oxaliplatin | 24.69% | 42.65% | 43.21% | 29.22% | 24.33% |
| | | PBS IX (pH = 5.0) Added (mL) | | | | | | |
| 0.5 | 0.0 | 4.5 | Oxaliplatin | 3.90% | 4.37% | 4.54% | 4.82% | 5.14% |
| 0.5 | 0.1 | 4.4 | Oxaliplatin | 15.46% | 26.44% | 28.95% | 28.86% | 21.47% |
| 0.5 | 0.2 | 4.3 | Oxaliplatin | 21.11% | 34.39% | 37.16% | 28.30% | 24.74% |
| 0.5 | 0.5 | 4.0 | Oxaliplatin | 26.06% | 41.75% | 45.62% | 30.94% | 28.13% |

Example 2

This example illustrates the enhanced cisplatin from therapeutic liposomes upon addition of different amounts of the attacking liposome. Therapeutic liposomes containing 2.5 mg/mL of cisplatin and 77.5 mg/mL of total lipids (NLICOV00AR-02, Northern Lipids Inc.) were prepared via a passive loading procedure. The attacking liposome consisting of DPPC, cholesterol, DOTAP, and TPGS (4460-075) was prepared as described in Example 1.

Figure 2:
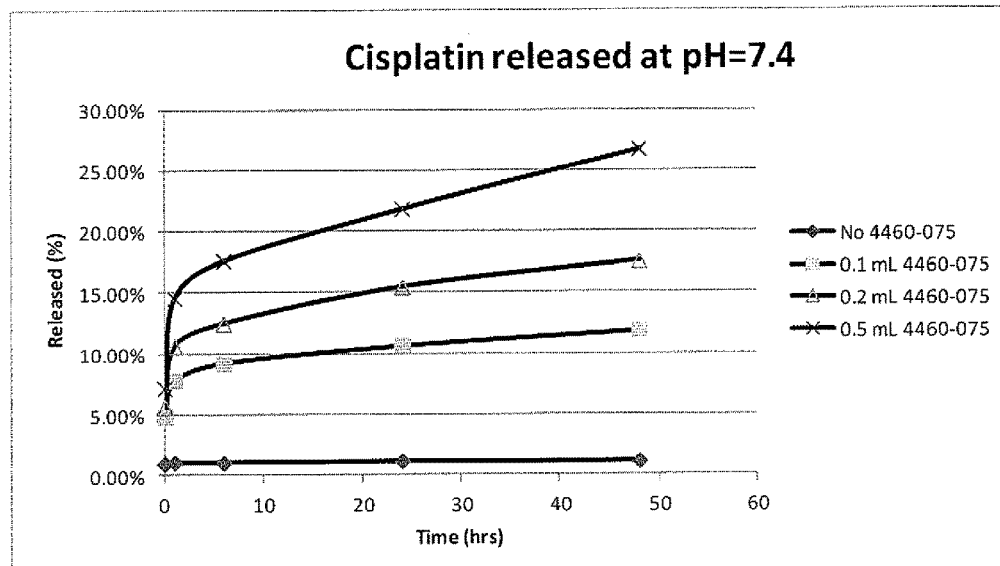
FIG. 2 shows cisplatin release from therapeutic liposomes triggered by varying amounts of attacking liposome 4460-075 at (a) pH=7.4 and (b) pH=5.
Figure 2:
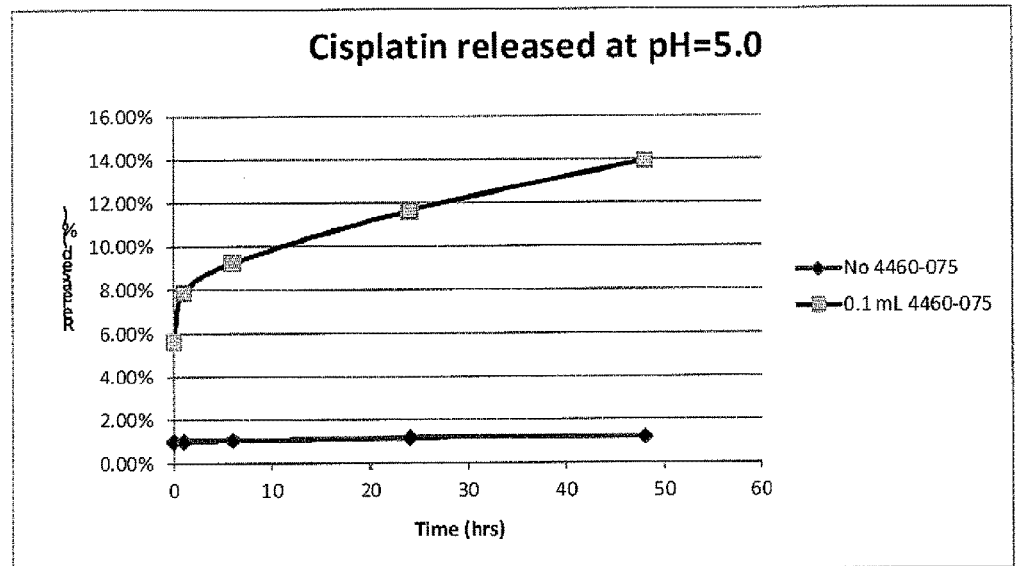

The in vitro cisplatin release from NLICOV00AR-02 was conducted in PBS 1× (pH=7.4 and 5.0) solutions by adding aliquots of attacking liposome (4460-075) to the therapeutic liposome. Samples were collected immediately at room temperature, and at 1, 6, 24 and 48 hours after incubation at 37° C. The samples were filtered through Amicon 50K MWCO centrifugal filters at 16500 rpm for 5 minutes. The cisplatin released in the liposome-free aqueous phase was analyzed by ICP-OES. The results are shown in Table 3 and 4. The data shown in Table 4 were plotted and shown in FIG. 2. The results indicate that the total release of therapeutic liposome (NLICOV00AR-02) at 48 hr was increased from ~1% without attacking liposome to ~27% with an equal amount of attacking liposome. The results also indicate that the total release of therapeutic liposome increased as the amount of attacking liposome increased at both pH conditions. In this example, the therapeutic liposome was a non-stealth, charged liposome containing 10 mol % cholesterol. The attacking liposome was oppositely charged and contained 32 mol % TPGS.

TABLE 3

Dualsome Components

| Dualsome | Name | Composition (mol %) | Particle Size (volume nm) | Zeta potential (mV) |
|---|---|---|---|---|
| Therapeutic liposome | NLICOV00AR-02 | DSPC/DSPG/Chol = 70/20/10 | 96.3 | −22.4 |
| Attacking liposome | 4460-075 | DPPC/Chol/TPGS/DOTAP = 42/10/32/16 | 80.3 | 11.4 |

TABLE 4

In-vitro release of Dualsome in PBS 1X (pH = 7.4 and pH = 5.0)

| Therapeutic Liposome (NLICOV00AR-02) Amount (mL) | Attacking Liposome (4460-075) Amount (mL) | PBS 1X (pH = 7.4) Added (mL) | Encapsulated Therapeutics | Immediate Release after mixing | Release at 1 hour | Release at 6 hour | Release at 24 hour | Release at 48 hour |
|---|---|---|---|---|---|---|---|---|
| 0.5 | 0.0 | 4.5 | Cisplatin | 0.97% | 1.05% | L05% | 1.13% | 1.11% |
| 0.5 | 0.1 | 4.4 | Cisplatin | 4.90% | 7.84% | 9.25% | 10.65% | 11.88% |
| 0.5 | 0.2 | 4.3 | Cisplatin | 5.68% | 10.63% | 12.47% | 15.45% | 17.55% |
| 0.5 | 0.5 | 4.0 | Cisplatin | 7.20% | 14.60% | 17.62% | 21.84% | 26.73% |
| | | PBS 5X (01 = 5.0) Added (mL) | | | | | | |
| 0.5 | 0.0 | 4.5 | Cisplatin | 1.01% | 1.02% | 1.05% | 1.16% | 1.20% |
| 0.5 | 0.1 | 4.4 | Cisplatin | 5.65% | 7.88% | 9.25% | 11.66% | 13.96% |

Example 3

In this example, the attacking liposome (Part B, 4460-075) consisted of DPPC, cholesterol, DOTAP, and TPGS as given in Table 5; the method of preparation was the same as described in Example 1. The therapeutic liposome (Part A, 4460-090) contained 5-carboxyfluorescein (5-CF) as a marker. The liposome containing 5-CF was made by the passive loading procedure as described below:

1. Lipid components were weighed and placed in a round bottom flask.
2. 3:1 (v/v) chloroform/methanol was added to dissolve all lipids; the concentration was about 2.5 wt %.
3. Solvents were removed from the lipid mixture using a rotoevaporator at 40° C., and vacuum was applied via the rotoevaporator for 0.5 hrs at 40° C. to remove residual solvents.
4. Drying was continued using the house vacuum overnight at room temperature to remove trace solvents.
5. Phosphate buffer saline (PBS) 1× solution (0.0067 M) was added to the dried lipid film around the bottom of the flask, and the resulting dispersion was agitated at 70° C. for one hour. In this step, 5-carboxyfluorescein (5-CF) was added to PBS at a concentration of 2.0 mg/mL. The pH value of the dispersion was adjusted to 7.10
6. The lipid vesicle dispersion was extruded 5 times through a double packed 200 nm polycarbonate film at 70° C. with a 10-mL extruder under a pressure of ~200 psi.
7. The extrusion was continued 10 times through a double packed 100 nm polycarbonate film at 70° C. under a pressure of ~300 psi.
8. The final liposome preparation was injected into a 3.0-12.0 mL 20,000 MWCO cassette for dialysis.
9. The liposome preparation was dialyzed against 1000 mL PBS 1× solution for 24 hours.
10. Dialysis was repeated two additional times with 1000 mL fresh PBS 1× buffer.
11. The dialyzed liposomes were collected, and particle size and zeta potential were measured using a Malvern Zetasizer Nano ZS.

Liposome Part A was mixed with Part B and the release of 5-CF to the liposome-free aqueous phase was determined by an Agilent 1200 HPLC with a Waters 2475 Multi-Wavelength Fluorescence Detector (S/N 608975406M). The column was a BDS Hypersil C18 column (150 mm×3.0 μm, Thermo Scientific, S/N: 0908389T, Lot #10770). The mobile phase consisted of 5% (wt) IPA/5% (wt) ACN/90% (wt) water with 50 mM Ammonium acetate. No gradient was applied. The flow rate was 0.8 mL/min at 40° C. The injection volume was 5.0 μL. The run time was set to 5 minutes, and the CF-5 eluted at ~1.0 min. For fluorescence detection, an excitation wavelength of 492 nm and an emission wavelength of 514 nm were used. The EUFS was set to 50,000 and the gain was set to 1.0 on the detector. External standards of CF-5 in PBS 1× were used for calibration. The linear calibration range was from 0.05 µg/mL to 2.0 µg/mL, resulting in an $R^2$ value greater than 0.99.

Figure 3:
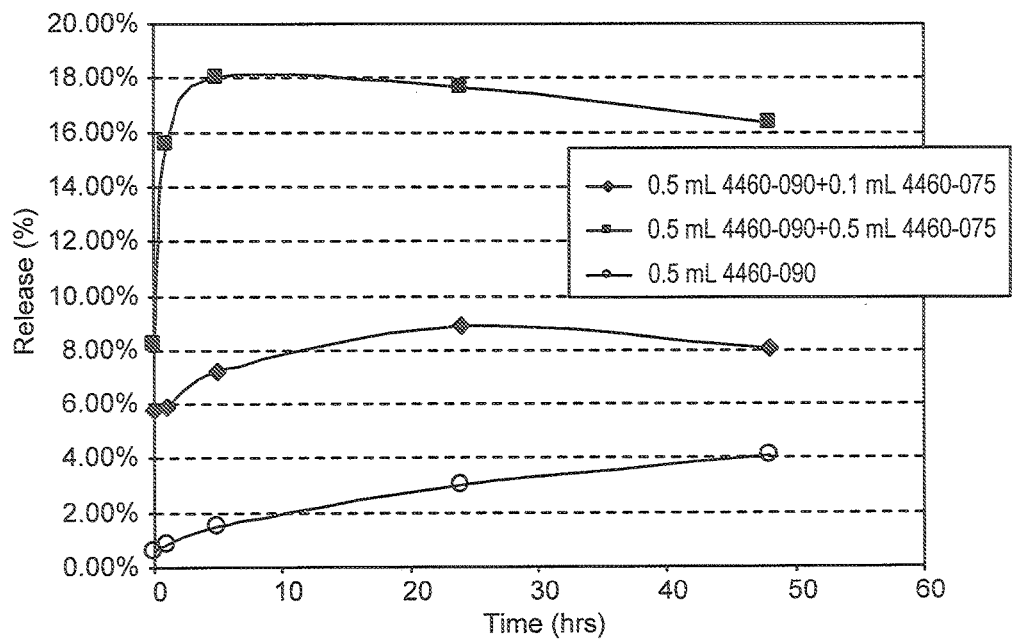
FIG. 3 shows the release of 5-carboxyfluorescein (5-CF) from therapeutic liposome Part A (4460-090) by adding attacking liposome Part B (4460-075) at pH=7.4.

The results shown in Table 6 and plotted in FIG. 3 indicate the total release of therapeutic liposome (4460-090) at 48-hours increased from ~4% to ~16% by the addition of an equal amount of attacking liposome (4460-075) in PBS 1× at pH 7.4. The results also suggest the release of therapeutic liposome increased with the increasing initial amount of attacking liposome. In this example, liposome Part A was a non-stealth charged liposome containing 40 mol % cholesterol. The attacking liposome, Part B, was oppositely charged and contained TPGS.

TABLE 5

Dualsome Components

| Dualsome | Name | Composition (mol %) | Particle Size (volume nm) | Zeta potential (mV) |
|---|---|---|---|---|
| Therapeutic liposome | 4460-090 | DSPC/DSPG/Chol = 48/12/40 | 109.2 | −17.4 |
| Attacking liposome | 4460-075 | DPPC/Cho1/TPGS/DOTAP = 42/10/32/16 | 80.3 | 11.4 |

TABLE 6

In-vitro release of Dualsome in PBS 1X (pH = 7.4)

| Therapeutic Liposome (4460-090) Amount (mL) | Attacking Liposome (4460-075) Amount (mL) | PBS 1X (pH = 7.4) Added (mL) | Encapsulated Therapeutics | Immediate Release after mixing | Release at 1 hour | Release at 6 hour | Release at 24 hour | Release at 48 hour |
|---|---|---|---|---|---|---|---|---|
| 0.5 | 0.0 | 9.5 | 5-CF | 0.60% | 0.85% | 1.50% | 2.98% | 4.07% |
| 0.5 | 0.1 | 9.4 | 5-CF | 5.78% | 5.87% | 7.23% | 8.92% | 8.08% |
| 0.5 | 0.5 | 4.0 | 5-CF | 8.25% | 15.56% | 18.04% | 17.66% | 16.33% |

Example 4

In this example, therapeutic liposome Part A (4460-077) contained 5-CF (5-carboxyfluorescein) as the marker, and the lipid composition was the same as the therapeutic liposome composition in Examples 1 and 2. The composition of the attacking liposome, Part B, was the same as in Examples 1 and 2 (see Table 7).

(4460-075) in PBS 1× at pH 7.4. The results also show that the release of 5-CF from liposome Part A increased as the initial amount of liposome Part B increased. These results are consistent with the finding as described in Example 1 and 2. In this example, liposome Part A was a non-stealth, charged liposome containing 10 mol % cholesterol. The attacking liposome Part B was oppositely charged and contained TPGS.

TABLE 7

Dualsome Components

| Dualsome | Name | Composition (mol %) | Particle Size (volume nm) | Zeta potential (mV) |
|---|---|---|---|---|
| Therapeutic liposome | 4460-077 | DSPC/DSPG/Chol = 70/20/10 | 88.1 | −20.5 |
| Attacking liposome | 4460-075 | DPPC/Chol/TPGS/DOTAP = 42/10/32/16 | 80.3 | 11.4 |

TABLE 8

In-vitro release of Dualsome in PBS 1X (pH = 7.4)

| Therapeutic Liposome (4460-077) Amount (mL) | Attacking Liposome (4460.075) Amount (mL) | PBS IX (pH = 7.4) Added (mL) | Encapsulated Therapeutics | Immediate Release after mixing | Release at 1 hour | Release at 6 hour | Release at 24 hour | Release at 48 hour |
|---|---|---|---|---|---|---|---|---|
| 0.5 | 0.0 | 9.5 | 5-CF | 2.69% | 3.04% | 3.42% | 4.25% | 5.34% |
| 0.5 | 0.1 | 9.4 | 5-CF | 16.58% | 24.75% | 26.48% | 30.84% | 29.36% |
| 0.5 | 0.5 | 4.0 | 5-CF | 13.08% | 24.96% | 26.08% | 30.36% | 32.48% |

Figure 4:
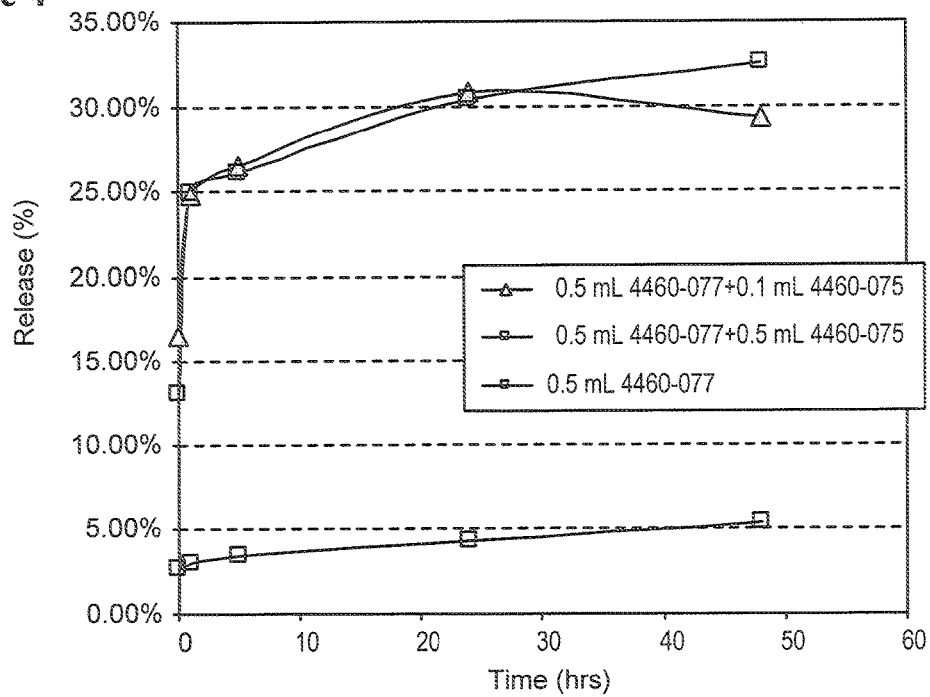
FIG. 4 shows the release of 5-CF from liposome Part A (4460-077) by mixing with liposome Part B (4460-075).

The results shown in Table 8 and plotted in FIG. 4 indicate that the total release of 5-CF from liposome Part A (4460-077) at 48 hours increased from ~5% to ~32% by the addition of an equal amount of attacking liposome Part B Example 5

In this example, liposome Part A (4386-143) was loaded with 5-carboxyfluorescein (5-CF) in the interior aqueous phase as in Examples 3 and 4. The compositions of liposome Part A and B (4460-075) are given Table 9.

Figure 5:
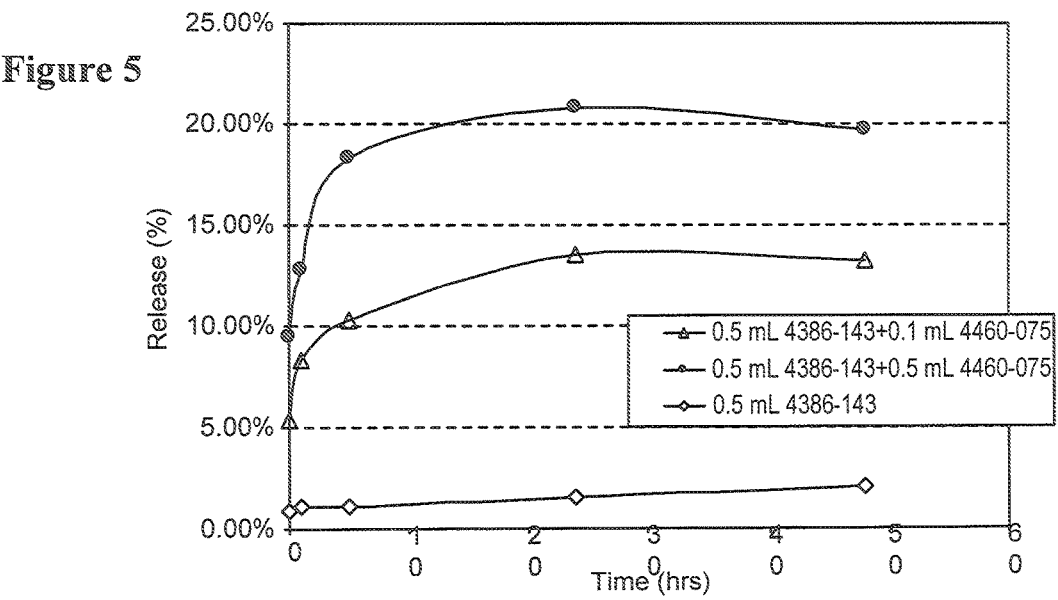
FIG. 5 shows the release of 5-CF from liposome Part A (4386-143) by mixing with liposome Part B (4460-075) at pH=7.4.

The results shown in Table 10 and plotted in FIG. 5 indicate that the total release of 5-CF from liposome Part A (4386-143) at 48 hours increased from ~2% to ~20% by the addition of an equal amount of attacking liposome Part B (4460-075) in PBS 1× at pH 7.4. The results also show the release of liposome Part A increased as the initial amount of attacking liposome Part B increased. In this example, the therapeutic liposome was a stealth liposome containing 40 mol % cholesterol. The attacking liposome was oppositely charged and contained TPGS.

1× at pH 7.4. In this example, the therapeutic liposome was a non-stealth liposome containing 40 mol % cholesterol. The attacking liposome was oppositely charged but did not include TPGS.

This example clearly illustrates the necessity of a triggering agent like TPGS in the attacking liposome composition in order to trigger the release of liposome Part A. Without TPGS, essentially, there was no enhanced release observed as shown in this example.

TABLE 9

Dualsome Components

| Dualsome | Name | Composition (mol %) | Particle Size (volume nm) | Zeta potential (mV) |
|---|---|---|---|---|
| Therapeutic liposome | 4386-143 | DSPC/Chol/DSPE-PEG(2000) = 55/40/5 | 91.1 | −0.87 |
| Attacking liposome | 4460-075 | DPPC/Chol/TPGS/DOTAP = 42/10/32/16 | 80.3 | 11.4 |

TABLE 11

Dualsome Components

| Dualsome | Name | Composition (mol %) | Particle Size (volume nm) | Zeta potential (mV) |
|---|---|---|---|---|
| Therapeutic liposome | 4460-090 | DSPC/DSPG/Chol = 48/12/40 | 109.2 | −17.4 |
| Attacking liposome | 4460-084 | DPPC/Chol/DOTAP = 73/11/16 | 91.56 | 23.0 |

TABLE 10

In-vitro release of Dualsome in PBS 1X (pH = 7.4)

| Therapeutic Liposome (4386-143) Amount (mL) | Attacking Liposome (4460-075) Amount (mL) | PBS 1X (pH = 7.4) Added (mL) | Immediate Release after mixing | Release at 1 hour | Release at 6 hour | Release at 24 hour | Release at 48 hour | Immediate Release after mixing |
|---|---|---|---|---|---|---|---|---|
| 0.5 | 0.0 | 9.5 | 5-CE | 0.92% | 1.10% | 1.07% | 1.58% | 2.04% |
| 0.5 | 0.1 | 9.4 | 5-CF | 5.40% | 8.32% | 10.26% | 13.52% | 13.25% |
| 0.5 | 0.5 | 4.0 | 5-CF | 9.50% | 12.82% | 18.30% | 20.80% | 19.72% |

Example 6

Figure 6:
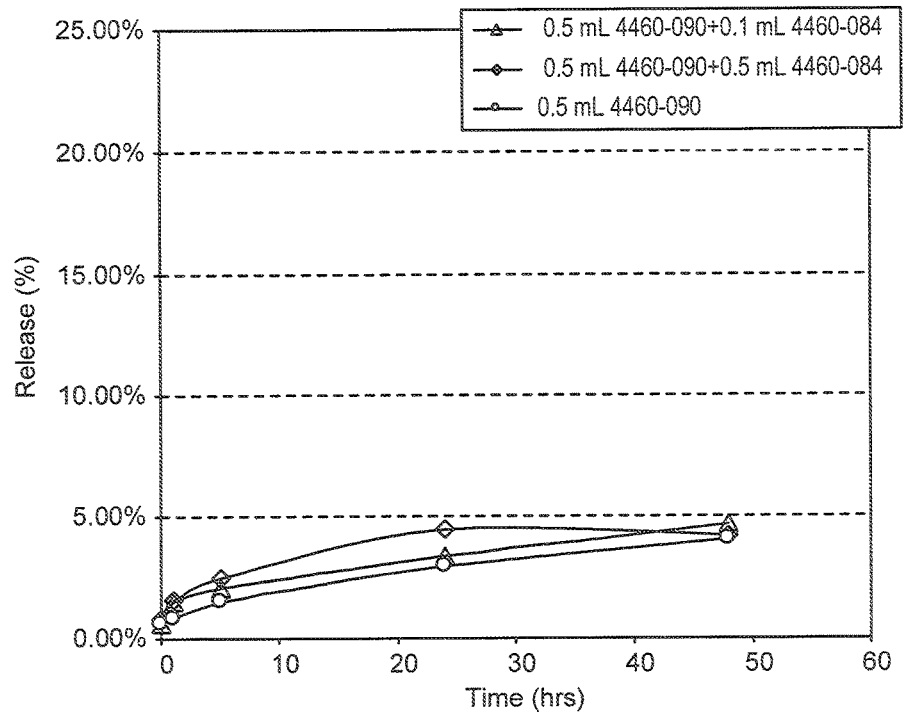
FIG. 6 shows the release of 5-CF from liposome Part A (4460-090) by mixing with liposome Part B (4460-084) at pH=7.4.

In this example, the compositions of liposome Part A and B are shown in Table 11. The therapeutic liposome Part A (4460-090) contained 5-CF. It should be noted that the attacking liposome, Part B (4460-084), did not include triggering agent TPGS in the composition. The results shown in Table 12 and plotted in FIG. 6 indicate that the total release of liposome Part A (4460-090) was not affected by the addition of attacking liposome Part B (4460-084) in PBS

TABLE 12

In-vitro release of Dualsome in PBS 1X (pH = 7.4)

| Therapeutic Liposome (4460-090) Amount (mL) | Attacking Liposome (4460-084) Amount (mL) | PBS IX (pH = 7.4) Added (mL) | Encapsulated Therapeutics | Immediate Release after mixing | Release at 1 hour | Release at 6 hour | Release at 24 hour | Release at 48 hour |
|---|---|---|---|---|---|---|---|---|
| 0.5 | 0.0 | 9.5 | 5-CF | 0.60% | 0.85% | 1.50% | 2.98% | 4.07% |
| 0.5 | 0.1 | 9.4 | 5-CF | 0.60% | 1.51% | 2.08% | 3.34% | 4.67% |
| 0.5 | 0.5 | 4.0 | 5-CF | 0.83% | 1.60% | 2.45% | 9.45% | 4.19% |

Example 7

Figure 7:
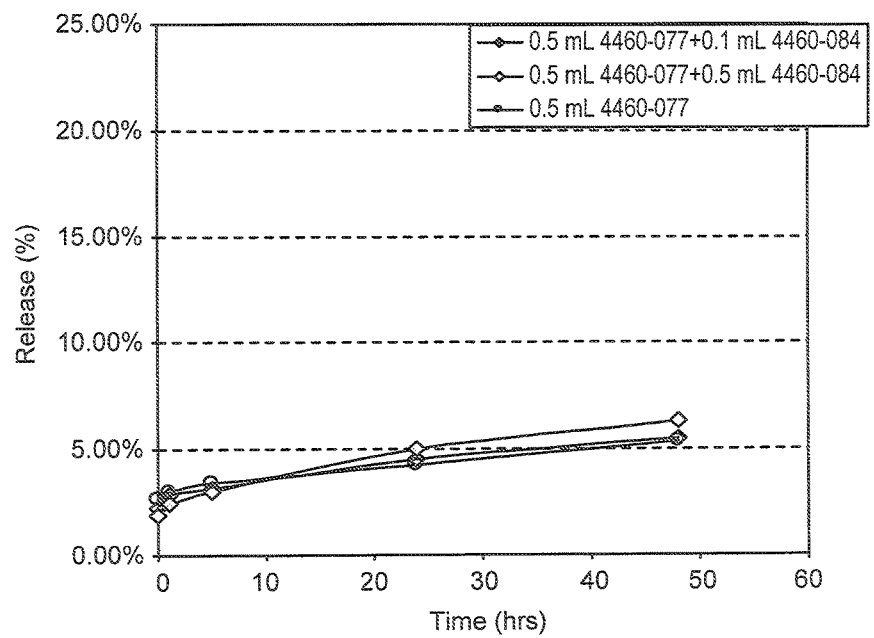
FIG. 7 shows the release of 5-CF from liposome Part A (4460-077) by mixing with liposome Part B (4460-084) at pH=7.4.

In this example, the compositions of liposome Part A and B are shown in Table 13. The therapeutic liposome Part A (4460-077) contained 5-CF. It should be noted that the attacking liposome, Part B (4460-084), did not contain triggering agent TPGS in the composition. The results shown in Table 14 and plotted in FIG. 7 indicate the total release of liposome Part A (4460-077) was not affected by the addition of attacking liposome Part B (4460-084) in PBS 1× at pH 7.4. In this example, the therapeutic liposome was a non-stealth liposome containing 10 mol % cholesterol. The attacking liposome was oppositely charged but without TPGS. Without TPGS in Part B, there was no enhanced release observed for Part A as shown in this example.

TABLE 13

Dualsome Components

| Dualsome | Name | Composition (mol %) | Particle Size (volume nm) | Zeta potential (mV) |
|---|---|---|---|---|
| Therapeutic liposome | 4460-077 | DSPC/DSPG/Chol = 70/20/10 | 88.1 | −20.5 |
| Attacking liposome | 4460-084 | DPPC/Chol/DOTAP = 73/11/16 | 91.56 | 23.0 |

TABLE 14

In-vitro release of Dualsome in PBS 1X (pH = 7.4)

| Therapeutic Liposome (4460-077) Amount (mL) | Attacking Liposome (4460-084) Amount (mL) | PBS 1X (pH = 7.4) Added (mL) | Encapsulated Therapeutics | Immediate Release after mixing | Release at 1 hour | Release at 6 hour | Release at 24 hour | Release at 48 hour |
|---|---|---|---|---|---|---|---|---|
| 0.5 | 0.0 | 9.5 | 5-CF | 2.69% | 3.04% | 3.42% | 4.25% | 5.34% |
| 0.5 | 01 | 9.4 | 5-CF | 2.23% | 2.86% | 3.18% | 4.53% | 5.47% |
| 0.5 | 0.5 | 4.0 | 5-CF | 1.94% | 2.51% | 3.04% | 4.99% | 6.34% |

Example 8

Figure 8:
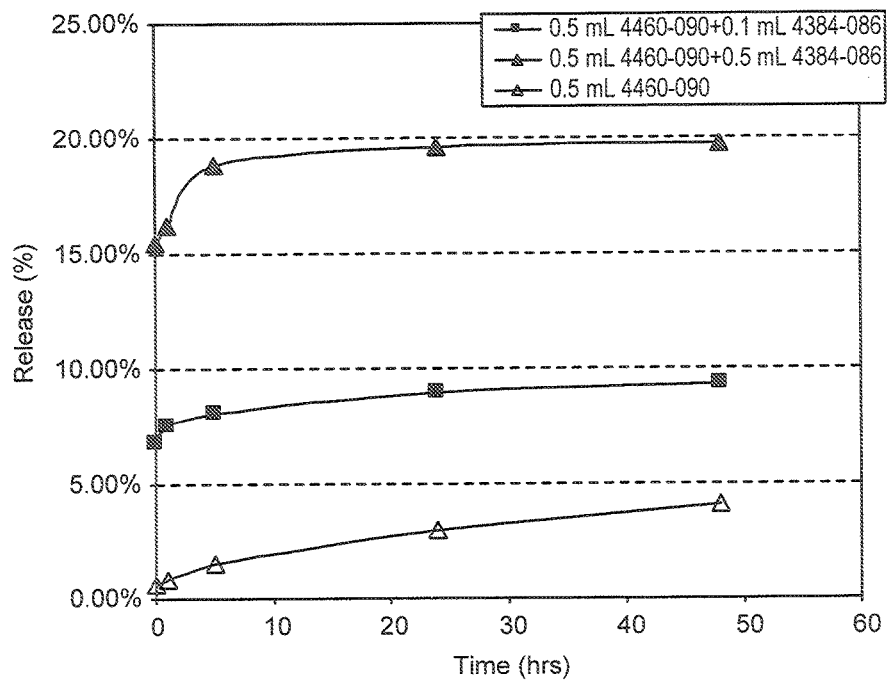
FIG. 8 shows the release of 5-CF from liposome Part A (4460-090) by mixing with liposome Part B (4384-086) at pH=7.4.

In this example, the compositions liposome Part A and B are shown in Table 15. The therapeutic liposome Part A (4460-090) contained 5-CF which is the same as in Example 6. The attacking liposome (4384-086) did not contain positively charged lipid DOTAP, but contained 30 mol % TPGS. The results shown in Table 16 and plotted in FIG. 8 indicate that the total release of 5-CF at 48-hours from liposome Part A (4460-090) in PBS 1× at pH 7.4 increased from ~4% to ~20% by the addition of an equal amount of attacking liposome. The results also indicate 5-CF release from therapeutic liposome increased with the increasing initial amount of the attacking liposome. The therapeutic liposome was a stealth liposome containing 40 mol % cholesterol level.

TABLE 15

Dualsome Components

| Dualsome | Name | Composition (mol %) | Particle Size (volume nm) | Zeta potential (mV) |
|---|---|---|---|---|
| Therapeutic liposome | 4460-090 | DSPC/DSPG/Chol = 48/12/40 | 109.2 | −17.4 |
| Attacking liposome | 4384-086 | DPPC/Chol/TPGS = 60/10/30 | 92.67 | 5.51 |

TABLE 16

In-vitro release of Dualsome in PBS 1X (pH-7.4)

| Therapeutic Liposome (4460-090) Amount (mL) | Attacking Liposome (4384-086) Amount (mL) | PBS 1X (pH = 7.4) Added (mL) | Encapsulated Therapeutics | Immediate Release after mixing | Release at 1 hour | Release at 6 hour | Release at 24 hour | Release at 48 hour |
|---|---|---|---|---|---|---|---|---|
| 0.5 | 0.0 | 9.5 | 5-CF | 0.60% | 0.85% | 1.50% | 2.98% | 4.07% |
| 0.5 | 0.1 | 9.4 | 5-CF | 6.77% | 7.53% | 8.07% | 8.99% | 9.34% |
| 0.5 | 0.5 | 4.0 | 5-CF | 15.44% | 16.20% | 18.87% | 19.64% | 19.74% |

Example 9

Figure 9:
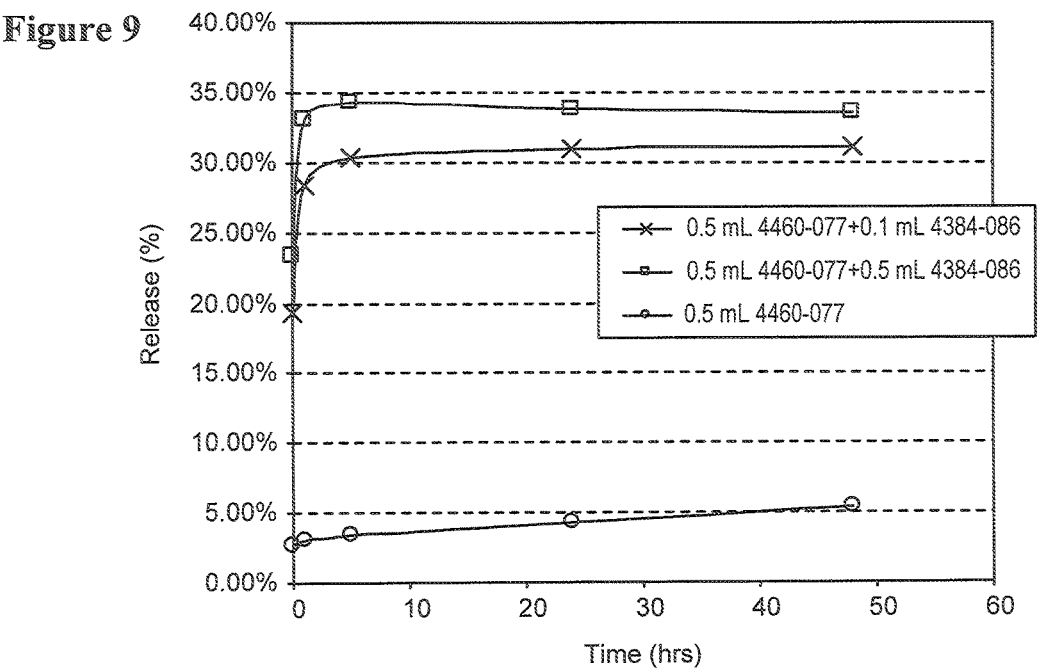
FIG. 9 shows the release of 5-CF from liposome Part A (4460-077) by mixing with liposome Part B (4384-086) at pH=7.4.

In this example, the compositions of liposome Part A and B are shown in Table 17. The therapeutic liposome Part A (4460-077) contained 5-CF which is the same as in Example 4. The therapeutic liposome was a stealth liposome containing 10 mol % cholesterol. The attacking liposome Part B (4460-086) contained 30 mole % TPGS in the composition and no charged lipid DOTAP, as in Example 5. The results shown in Table 18 and plotted in FIG. 9 indicate that the total release of 5-CF at 48 hours from liposome (4460-077) increased from ~5% to ~34% by the addition of an equal amount of attacking liposome (4384-086) in PBS 1× at pH 7.4. The results also indicate that 5-CF release from liposome (4460-077) increased with the increasing initial amount of attacking liposome.

release of liposome (4460-090) increased with the increasing initial amount of the attacking liposome.

TABLE 17

Dualsome Components

| Dualsome | Name | Composition (mol %) | Particle Size (volume nm) | Zeta potential (mV) |
|---|---|---|---|---|
| Therapeutic liposome | 4460-077 | DSPC/DSPG/Chol = 70/20/10 | 88.1 | −20.5 |
| Attacking liposome | 4384-086 | DPPC/Chol/TPGS = 60/10/30 | 92.67 | 5.51 |

TABLE 18

In-vitro release of Dualsome in PBS 1X (pH = 7.4)

| Thempeutic Liposome (4460-077) Amount (mL) | Attacking Liposome (4384-086) Amount (mL) | PBS 1X (pH = 7.4) Added (mL) | Encapsulated Therapeutics | Immediate Release after mixing | Release at 1 hour | Release at 6 hour | Release at 24 hour | Release at 48 hour |
|---|---|---|---|---|---|---|---|---|
| 0.5 | 0.0 | 9.5 | 5-CF | 2.69% | 3.04% | 3.42% | 4.25% | 5.34% |
| 0.5 | 0.1 | 9.4 | 5-CF | 19.30% | 28.36% | 30.29% | 30.94% | 31.05% |
| 0.5 | 0.5 | 4.0 | 5-CF | 23.40% | 33.00% | 34.29% | 33.81% | 33.55% |

Example 10

Figure 10:
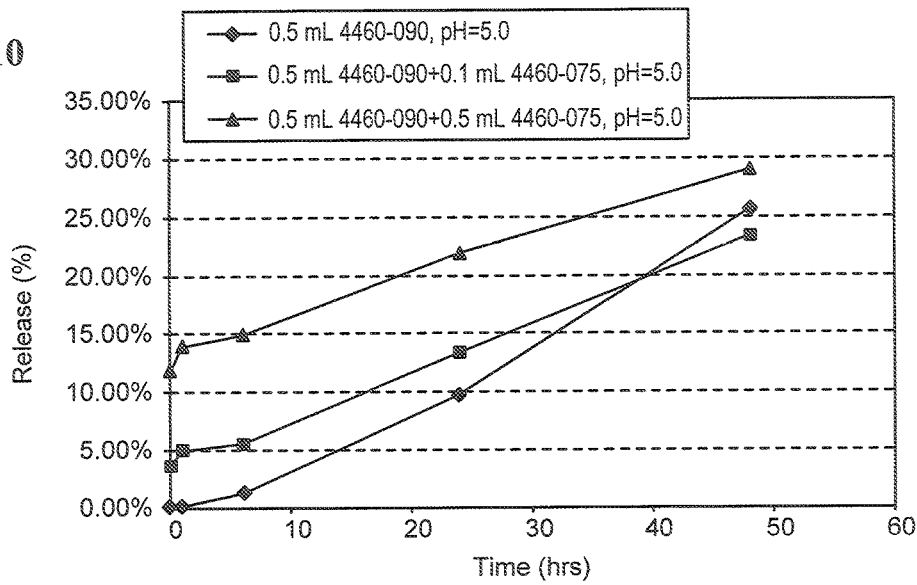
FIG. 10 shows the release of 5-CF from liposome Part A (4460-090) by mixing with liposome Part B (4460-075) at pH=5.0.

In this example, the compositions of liposome Part A and B are shown in Table 19. The therapeutic liposome Part A (4460-090) contained 5-CF, as in Example 6. The therapeutic liposome was a non-stealth liposome containing 40 mol % cholesterol. The attacking liposome Part B (4460-075) contained 32 mole % TPGS and 16 mole % DOTAP, providing positive charges to the attacking liposome. The results shown in Table 20 and plotted in FIG. 10 indicate the total release of 5-CF from the therapeutic liposome (4460-090) increased from ~5% to ~26% with the addition of attacking liposome (4460-075) even when the pH value was changed from 7.4 to 5.0. The results clearly show the total

TABLE 19

Dualsome Components

| Dualsome | Name | Composition (mol %) | Particle Size (volume nm) | Zeta potential (mV) |
|---|---|---|---|---|
| Therapeutic liposome | 4460-090 | DSPC/DSPG/Chol = 48/12/40 | 109.2 | −17.4 |
| Attacking liposome | 4460-075 | DPPC/Chol/TPGS/DOTAP = 42/10/32/16 | 80.3 | 11.4 |

TABLE 20

In-vitro release of Dualsome in PBS 1X (pH = 5.0)

| Therapeutic Liposome (4460-090) Amount (mL) | Attacking Liposome (4460-075) Amount (mL) | PBS 1X (pH = 5.0) Added (mL) | Encapsulated Therapeutics | Immediate Release after mixing | Release at 1 hour | Release at 6 hour | Release at 24 hour | Release at 48 hour |
|---|---|---|---|---|---|---|---|---|
| 0.5 | 0.0 | 9.5 | 5-CF | 0 | 0 | 1.18% | 9.72% | 25.60% |
| 0.5 | 0.1 | 9.4 | 5-CF | 3.61% | 4.94% | 5.40% | 13.35% | 23.37% |
| 0.5 | 0.5 | 4.0 | 5-CF | 11.88% | 13.87% | 14.89% | 21.92% | 29.02% |

Example 11

Figure 11:
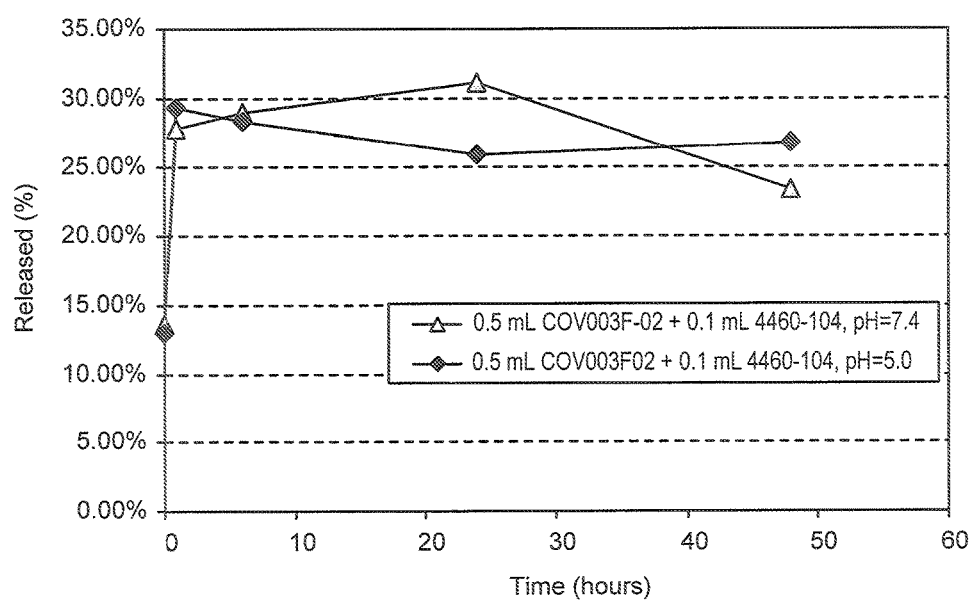
FIG. 11 shows the release of oxaliplatin from liposome (NLICOV003F-02) by adding attacking liposome 4460-104 at pH=7.4 and pH=5.0.

In this example, the compositions of liposome Part A and B are shown in Table 21. The therapeutic liposome (NLICOV003F-02) contained Oxaliplatin, as in Example 1. The therapeutic liposome was a non-stealth liposome containing 10 mol % cholesterol. The attacking liposome (4460-104) contained 32 mol % TPGS and 16 mol % DOTAP, providing positive charges to the attacking liposome. The results shown in Table 22 and plotted in FIG. 11 indicate the total release of therapeutic liposome (COV003F-02) at 48-hours increased from ~5% to ~25% by addition of 20% of attacking liposome (4460-104) in PBS 1× at both pH 7.4 and pH 5.0.

TABLE 21

Dualsome Components

| Dualsome | Name | Composition (mol %) | Particle Size (volume nm) | Zeta potential (mV) |
|---|---|---|---|---|
| Therapeutic liposome | NLICOV003E-02 | DSPC/DSPG/Chol = 70/20/10 | 83.6 | −22.6 |
| Attacking liposome | 4460-104 | DPPC/Chol/TPGS/DOTAP = 42/10/32/16 | 76.5 | 5.89 |

TABLE 22

In-vitro release of Dualsome in PBS 1X (pH = 5.0)

| Therapeutic Liposome (COV003F-02) Amount (mL) | Attacking Liposome (4460-104) Amount (mL) | PBS IX Added (mL) | Encapsulated Therapeutics | Immediate Release after mixing | Release at 1 hour | Release at 6 hour | Release at 24 hour | Release at 48 hour |
|---|---|---|---|---|---|---|---|---|
| 0.5 | 0.1 | 4.4, pH = 7.4 | Oxaliplatin | 13.59% | 27.78% | 28.95% | 31.12% | 23.45% |
| 0.5 | 0.1 | 4.4, pH = 5.0 | Oxaliplatin | 12.93% | 29.32% | 28.37% | 25.97% | 26.78% |

Example 12

Figure 12:
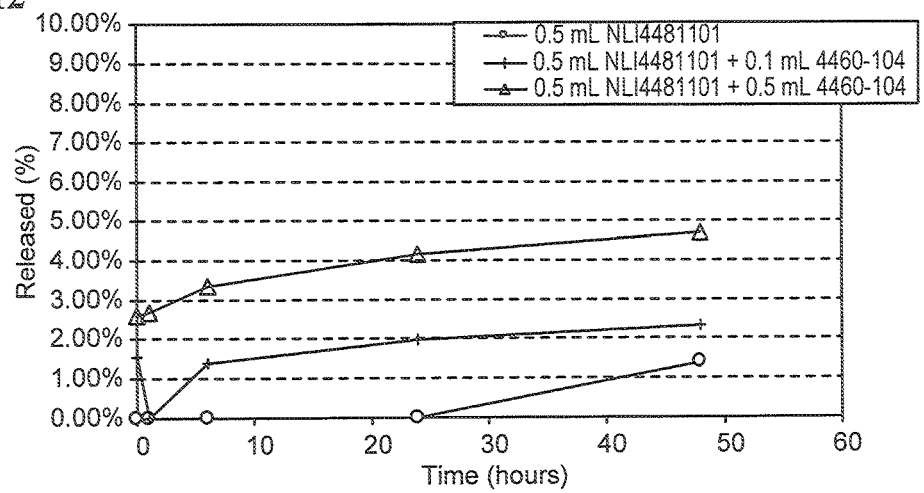
FIG. 12 shows the release of cisplatin from therapeutic liposomes (NLI 4481101) by adding attacking liposomes (4460-104) at (a) pH=5.0 and (b) pH=7.4.
Figure 12:
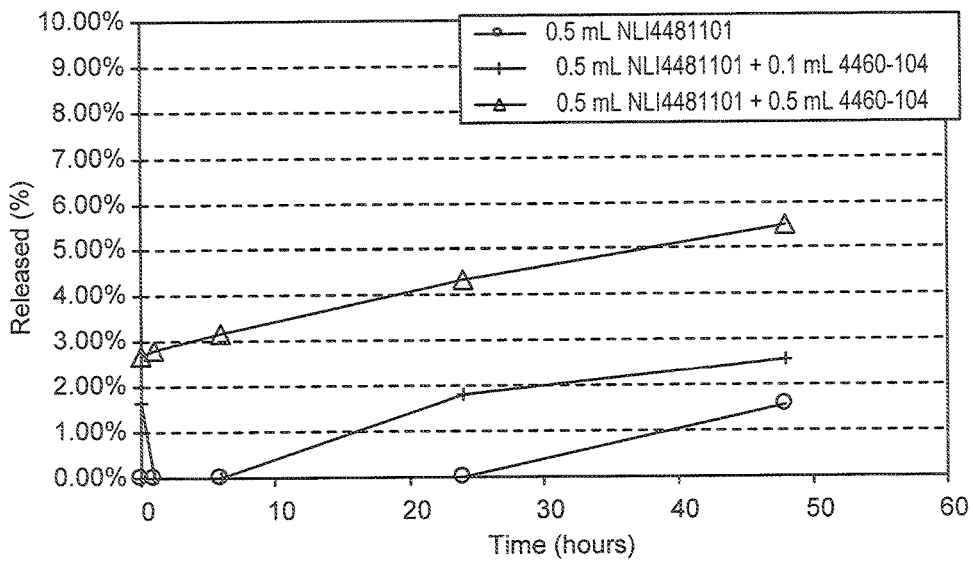

In this example, the compositions of liposome Part A and B are shown in Table 23. The therapeutic liposome (NLI 4481101) contained cisplatin. The therapeutic liposome was a stealth liposome with 40 mol % cholesterol. The attacking liposome (4460-104) contained 32 mol % TPGS and 16 mol % DOTAP, providing positive charges to the attacking liposome. The results shown in Table 23 and plotted in FIG. 12 indicate the release of therapeutic liposome (NLI4481101) after 48 hours increased from ~1% to ~5% by the addition of attacking liposome (4460-104) in PBS 1× at both pH 7.4 and pH 5.0. The results also indicate the cisplatin release of therapeutic liposome increased with the increasing amount of the attacking liposome. The therapeutic liposome was a stealth liposome containing 40 mol % cholesterol. The attacking liposome was oppositely charged, and contained 32 mol % TPGS.

TABLE 23

Dualsome Components

| Dualsome | Name | Composition (mol %) | Particle Size (volume nm) | Zeta potential (mY) |
|---|---|---|---|---|
| Therapeutic liposome | NL1 4481101 | HSPC/Chol/DSPE-PEG(2000) = 55/40/5 | 107.1 | −0.99 |
| Attacking liposome | 4460-104 | DPPC/Chol/TPGS/DOTAP = 42/10/32/16 | 76.5 | 5.89 |

TABLE 24

In-vitro release of Dualsome at PBS 1X (pH-7.4 and pH = 5.0)

| Therapeutic Liposome (NL14481101) Amount (mL) | Attacking Liposome (4460-104) Amount (mL) | PBS IX (pH = 7.4) Added (mL) | Encapsulated Therapeutics | Immediate Release after mixing | Release at 1 hour | Release at 6 hour | Release at 24 hour | Release at 48 hour |
|---|---|---|---|---|---|---|---|---|
| 0.5 | 0.0 | 4.5 | Cisplatin | 0 | 0 | 0 | 0 | 1.39% |
| 0.5 | 0.1 | 4.4 | Cisplatin | 1.55% | 0 | 1.39% | 1.98% | 2.34% |
| 0.5 | 0.5 | 4.0 | Cisplatin | 2.61% | 2.67% | 3.32% | 4.17% | 4.70% |

| Therapeutic Liposome (NLICOV003F-02) Amount (mL) | Attacking Liposome (4460-075) Amount (mL) | PBS IX (pH = 5.0) Added (mL) | Encapsulated Therapeutics | Immediate Release after mixing | Release at 1 hour | Release at 6 hour | Release at 24 hour | Release at 48 hour |
|---|---|---|---|---|---|---|---|---|
| 0.5 | 0.0 | 4.5 | Cisplatin | 0 | 0 | 0 | 0 | 1.56% |
| 0.5 | 0.1 | 4.4 | Cisplatin | 1.64% | 0 | 0 | 1.79% | 2.56% |
| 0.5 | 0.5 | 4.0 | Cisplatin | 2.68% | 2.83% | 3.18% | 4.35% | 5.50% |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A first composition comprising a first liposome comprising a therapeutic agent, wherein the therapeutic agent is selected from the group consisting of: cisplatin, oxaliplatin, carboplatin, gemcitibine, 5-fluorouracil, doxorubicin, and a taxane; and a second composition comprising a lipid nanoparticle comprising a non-ionic triggering agent for sequential or concurrent use with the first composition in delivering a therapeutic agent to a subject in need thereof, whereby release of the therapeutic agent from the liposome following administration of the lipid nanoparticle is increased, relative to the release of the therapeutic agent from the liposome without administration of the lipid nanoparticle.

2. The first composition of claim 1, wherein the first liposome comprises one or more lipids selected from the group consisting of: a phospholipid, a steroid, and a cationic lipid.

3. The first composition of claim 2, wherein the phospholipid is selected from the group consisting of: a phophatidylcholine, a phosphatidylglycerol, a phosphatidylethanolamine, a phosphatidylserine, a phosphatidylinositol, and a phosphatidic acid.

4. The first composition of claim 3, wherein the phosphatidylcholine is di stearoyl phosphatidyl choline (DSPC).

5. The first composition of claim 3, wherein the phosphatidylglycerol is distearoyl phosphatidyl glycerol (DSPG).

6. The first composition of claim 3, wherein the phosphatidylethanolamine is DSPE-PEG(2000).

7. The first composition of claim 2, wherein the steroid is cholesterol.

8. The first composition of claim 2, wherein the cationic lipid is N-(1-)2,3-dioleoyloxy)propyl)-N,N,N-trimethylammonium chloride (DOTAP).

9. The second composition of claim 1, wherein the lipid nanoparticle is selected from the group consisting of: a second liposome, a micelle, and mixtures thereof.

10. The second composition of claim 9, wherein the lipid nanoparticle is a second liposome.

11. The second composition of claim 10, wherein the second liposome comprises one or more lipids selected from the group consisting of a phospholipid, a steroid, and a cationic lipid.

12. The second composition of claim 11, wherein the phospholipid is selected from the group consisting of: a phophatidylcholine, a phosphatidylglycerol, a phosphatidylethanolamine, a phosphatidylserine, a phosphatidylinositol, and a phosphatidic acid.

13. The second composition of claim 12, wherein the phosphatidylcholine is dipalmitoyl phosphatidyl choline (DPPC).

14. The second composition of claim 11, wherein the steroid is cholesterol.

15. The second composition of claim 11, wherein the cationic lipid is N-(1-)2,3-dioleoyloxy)propyl)-N,N,N-trimethylammonium chloride (DOTAP).

16. The second composition of claim 1, wherein the non-ionic triggering agent is D-α-tocopheryl polyethylene glycol succinate (TPGS).

17. The first composition and second composition of claim 1, wherein the first liposome comprises 40-80 mole % DSPC, 5-50 mole % cholesterol, 0-30 mole % DSPG, and 0-10 mole % DSPE-PEG(2000); and wherein the lipid nanoparticle is a second liposome comprising 40-70 mole % DPPC, 5-20 mole % cholesterol, 0-20 mole % DOTAP, and 20-40 mole % TPGS.

18. The first composition and second composition of claim 1, wherein the subject is human.

19. The first composition and second composition of claim 1, wherein the lipid nanoparticle is administered after the first liposome is administered and accumulated at a target site within the subject.

20. The first composition and second composition of claim 1, wherein administration of the lipid nanoparticle increases the release of the therapeutic agent from the first liposome at least 3-fold, 10-fold, or 25-fold relative to the administration of the first liposome without use of the lipid nanoparticle.

* * * * *